United States Patent
Hidaka et al.

[11] Patent Number: 6,153,608
[45] Date of Patent: Nov. 28, 2000

[54] ISOQUINOLINE DERIVATIVES AND DRUGS

[75] Inventors: Hiroyoshi Hidaka, Nagoya; Akira Matsuura, Shiga-gun; Takushi Matsuzaki, Nagaokakyo, all of Japan

[73] Assignee: Nippon Shinyaku Co., Ltd., Kyoto, Japan

[21] Appl. No.: 09/117,433

[22] PCT Filed: Jan. 31, 1997

[86] PCT No.: PCT/JP97/00240

§ 371 Date: Jul. 29, 1998

§ 102(e) Date: Jul. 29, 1998

[87] PCT Pub. No.: WO97/28130

PCT Pub. Date: Aug. 7, 1997

[30] Foreign Application Priority Data

Feb. 2, 1996 [JP] Japan ................................. 8-017946
Oct. 18, 1996 [JP] Japan ................................. 8-275886

[51] Int. Cl.[7] ........................ A61K 31/55; A61K 31/495; C07D 245/00; C07D 491/00; C07D 401/00; C07D 239/00; C07D 487/00; C07D 239/70; C07D 239/02

[52] U.S. Cl. ............................ 514/218; 514/218; 514/221; 514/247; 514/248; 514/249; 514/253.05; 514/258; 514/307; 540/470; 540/472; 540/556; 540/575; 540/577; 540/579; 540/597; 544/235; 544/238; 544/242; 544/253; 544/282; 544/316; 544/319; 544/349; 544/351; 544/363

[58] Field of Search ..................... 540/470, 472, 540/556, 575, 577, 579, 597; 544/235, 238, 242, 253, 282, 316, 319, 349, 351, 363; 546/146, 139, 141, 142; 514/218, 221, 247, 248, 249, 254, 258, 307, 253, 253.05

[56] References Cited

U.S. PATENT DOCUMENTS

| | | | |
|---|---|---|---|
| 4,456,757 | 6/1984 | Hidaka et al. | 546/139 |
| 4,634,770 | 1/1987 | Hidaka et al. | 546/145 |
| 4,678,783 | 7/1987 | Hidaka et al. | 514/218 |

Primary Examiner—Mukund J. Shah
Assistant Examiner—Ben Schroeder

[57] ABSTRACT

The invention relates to a compound of the following general formula [I] or a medicinally acceptable salt thereof, or a solvate thereof,

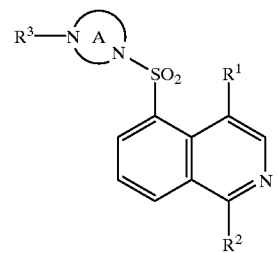

[I]

wherein $R^1$ represents alkyl, alkenyl, alkynyl, alkoxy, hydroxy, cyano, or halogen; $R^2$ represents hydrogen, hydroxy, or halogen; $R^3$ represents hydrogen, alkyl, or amidino; Ring A represents a 5 to 11-membered cyclic amino group which may be substituted, which cyclic amino group may be bridged between two carbon atoms in optional positions. The compound of this invention is useful for the prevention or treatment of cerebral tissue impairment due to the vasospasm following cerebral hemorrhage.

16 Claims, No Drawings

ISOQUINOLINE DERIVATIVES AND DRUGS

TECHNICAL FIELD

The present invention relates to an isoquinoline derivative having cerebral vasospasm-inhibiting activity and, thus, finding application as a medicine.

BACKGROUND ART

Cerebrovascular disease can be groupified into a hemorrhagic group and an ischemic group. The hemorrhagic group typically comprises subarachnoid hemorrhage arising from aneurysmal rupture, hypertensive cerebral hemorrhage, and head trauma. Subarachnoid hemorrhage entails a delayed vasospasm of the major cerebral arteries and may lead to vascular constriction disorders and sometimes to death. The ischemic group is represented by cerebral infarction and transient ischemic attack (TIA). The vascular disorder and neuronal injury caused by infarction or hemorrhage may lead to dyskinesia such as numbness or motor paralysis of the limbs and neurologic and mental dysfunctions in the acute through chronic stage, with disturbance of consciousness and death ensuing in severe cases.

For the treatment of such cerebrovascular diseases, antithrombotics and enhancers of cerebral circulation and metabolism have been used to this day. However, few drugs are available which inhibit this fatal cerebral vasospasm or the neuronal injury leading to dementia and there exists a pressing need for an effective therapeutic agent.

By way of illustration, as subarachnoid hemorrhage takes place, narrowing of the vascular lumen persisting for several weeks is induced in the major cerebral arteries in 4~5 days following the bleeding event. This phenomenon is known as cerebral vasospasm and once the ultimate ischemia triggers the onset of neurological symptoms, the functional prognosis and, at times, even the vital prognosis of the case are seriously influenced.

As the therapeutic drug for cerebral vasospasm subsequent to subarachnoid hemorrhage, fasudil [hexahydro-1-(5-isoquinolinylsulfonyl)-1H-1,4-diazepine] hydrochloride is the only drug that is used clinically today (Japanese Kokai Tokkyo Koho S61-227581).

Aside from the above drug, it is known that compounds having an isoquinoline ring substituted by cyclic aminosulfonyl in its 5-position are useful as cerebrovascular drugs (vasodilators, enhancers of cerebral circulation and metabolism, antianginal drugs, prophylactic and therapeutic drugs for cerebrovascular or cardiovascular thrombosis, and prophylactic and therapeutic drugs for hypertension) [Japanese Kokai Tokkyo Koho S57-156463, S58-121279, and S61-227581].

Not known, however, is a compound such that its isoquinoline skeleton has been substituted by a cyclic aminosulfonyl group in its 5-positon and further substituted in its 4-position.

DISCLOSURE OF THE INVENTION

The object of the invention is to provide a compound which is structurally novel, only sparingly toxic, and superior to any known drug as a prophylactic or therapeutic drug for cerebrovascular diseases, particularly as a cerebral vasospasm inhibitor.

To accomplish the above object, the inventors of the present invention synthesized and screened a large number of structurally new compounds and found that a compound of the following general formula [I] has very satisfactory cerebral vasospasm-reversing activity. The present invention has been developed on the basis of the above finding.

The present invention, therefore, is concerned with a compound of the following general formula [I] or a pharmaceutically acceptable salt thereof, or a solvate thereof, and a medicinal composition comprising it as an active ingredient,

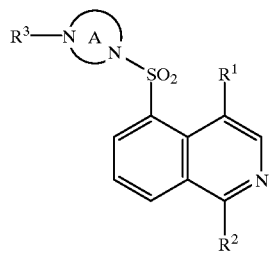

[I]

wherein $R^1$ represents alkyl, alkenyl, alkynyl, alkoxy, hydroxy, cyano, or halogen;

$R^2$ represents hydrogen, hydroxy, or halogen;

$R^3$ represents hydrogen, alkyl, or amidino;

Ring A represents a 5 to 11-membered cyclic amino group which maybe substituted, which cyclic amino group may be bridged between two carbon atoms in optional positions.

In chemical structure, the compound of the invention is characterized in that the 4-position of an isoquinoline skeleton is substituted by a substituent selected from the group consisting of alkyl, alkenyl, alkynyl, alkoxy, hydroxy, cyano, and halogen.

The present invention is now described in detail.

The "alkyl" in the context of the present invention includes straight-chain or branched alkyl groups of 1–6 carbon atoms, such as methyl, ethyl, n-propyl, isopropyl, n-butyl, isobutyl, sec-butyl, tert-butyl, n-pentyl, isopentyl, n-hexyl, and isohexyl. Among them, alkyl groups of 1 to 4 carbon atoms are preferred and methyl is particularly preferred.

The "alkenyl" includes straight-chain or branched alkenyl groups of 2 to 6 carbon atoms, such as vinyl, allyl, isopropenyl, methallyl, 2-butenyl, and 3-butenyl. Among them, alkenyl groups of 2 to 4 carbon atoms are preferred.

The "alkynyl" includes straight-chain or branched alkynyl groups of 2 to 6 carbon atoms, such as ethynyl, 1-propynyl, 2-propynyl, 1-butynyl, 2-butynyl, and 3-butynyl. Among them, alkynyl groups of 2 to 4 carbon atoms are preferred.

The "alkoxy" includes straight-chain or branched alkoxy groups of 1 to 4 carbon atoms, such as methoxy, ethoxy, n-propoxy, isopropoxy, n-butoxy, isobutoxy, sec-butoxy, and tert-butoxy.

The "halogen" includes chlorine, fluorine, bromine, and iodine.

Ring A includes saturated 5 to 11-membered monocyclic or bridged heterocyclic groups each containing 2 nitrogen atoms as ring-constituent hetero atoms. Thus, for example, imidazolidyl, piperazino, hexahydro-1H-1,4-diazepin-1-yl, 1,5-diazacyclooctan-1-yl, 3,6-diazabicyclo[3.2.2]nonan-3-yl, 3,6-diazabicyclo[3.2.1]octan-3-yl, 2,5-diazabicyclo[2.2.1]-heptan-2-yl, and 2,5-diazabicyclo[2.2.2]octan-2-yl can be mentioned. This Ring A may be substituted by 1–4 same or different substituent(s) selected from the group consisting of alkyl, halogen, phenyl, and aminoalkyl on its carbon atom or atoms.

$R^1$ is preferably $C_{1-4}$ alkyl, particularly methyl. $R^2$ is preferably hydrogen. $R^3$ is preferably hydrogen. Ring A is preferably a hexahydro-1H-1,4-diazepin-1-yl, particularly 2- or 7-methyl-hexahydro-1H-1,4-diazepin-1-yl.

The salt of compound [I] according to the invention includes salts with inorganic acids such as hydrochloric acid, sulfuric acid, nitric acid, phosphoric acid, hydrofluoric acid and hydrobromic acid, and salts with organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The compound [I] of the invention can be produced by, for example, the following procedure.

Process 1

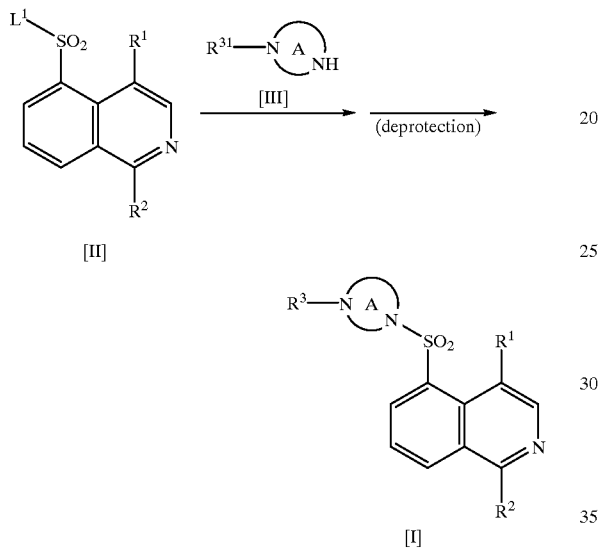

(wherein $R^1$, $R^2$, $R^3$, and Ring A are respectively as defined hereinbefore; $R^{31}$ means $R^3$ or represents a protective group; $L^1$ represents a leaving group)

The leaving group $L^1$ includes residues of the reactive derivatives of sulfonic acid to be mentioned hereinafter. The protective group $R^{31}$ includes acyl such as formyl, acetyl or benzoyl; aralkyloxycarbonyl such as benzyloxycarbonyl; alkoxycarbonyl such as tert-butyloxycarbonyl; and aralkyl such as benzyl.

An amine of general formula [III] is reacted with a sulfonic acid of general formula [II] or a reactive derivative thereof in a suitable solvent and, where necessary, the protective group is removed to provide compound [I]. The reaction solvent may be any solvent that does not interfere with the reaction, thus including ethers such as tetrahydrofuran, dioxane and diethyl ether; hydrocarbons such as benzene and toluene; halogenated hydrocarbons such as methylene chloride and chloroform; aprotic solvents such as N,N-dimethylformamide and N,N-dimethylacetamide; pyridine, acetonitrile, etc.; and mixtures of such solvents. The reactive derivative of sulfonic acid includes sulfonic acid halides (e.g. sulfonyl chloride and sulfonyl bromide), sulfonic anhydride, and N-sulfonylimidazolide, among others. Particularly preferred is a sulfonyl halide.

This reaction is preferably conducted in the presence of a base. The base includes various alkalies such as alkali metal hydrogencarbonates (e.g. sodium hydrogencarbonate), alkali metal carbonates (e.g. potassium carbonate), and alkali metal hydroxides (e.g. sodium hydroxide and potassium hydroxide) and organic tertiary amines such as triethylamine and triethylenediamine. When a basic solvent such as pyridine is used as the reaction solvent, said base need not be used. Therefore, a solvent of this kind can be used with advantage.

This reaction usually proceeds at room temperature but may optionally be conducted under cooling or heating, for example at −78–150° C., preferably 0–120°C. When a base is used, the amount of the reactive derivative [II] relative to amine [III] is preferably 1–10 molar equivalents and more preferably 1–3 molar equivalents. The amount of the base relative to amine [III] is preferably 1–10 molar equivalents and more preferably 1–3 equivalents. When the base is not used, the amount of said or reactive derivative [II] relative to amine [III] is equimolar or less and preferably in the range of 0.5–0.1 molar equivalents. The reaction time is dependent on the species of starting compounds and solvent used, reaction temperature, and other conditions but is generally 5 minutes to 70 hours. Where necessary, the protective group is removed by a per se known procedure after completion of the reaction.

Process 2

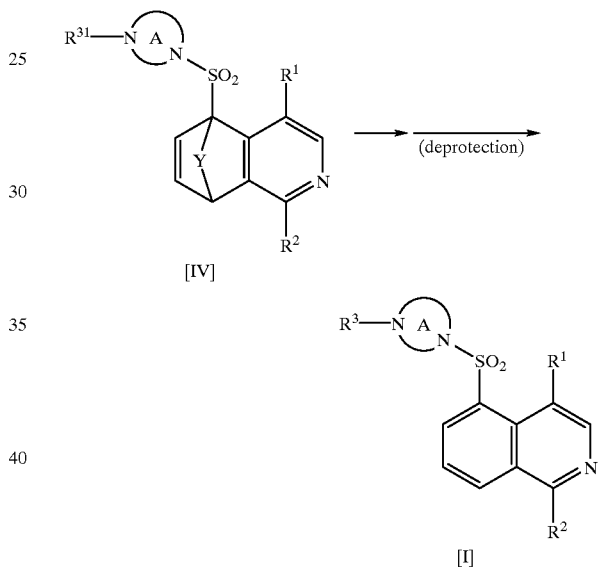

(wherein $R^1$, $R^2$, $R^3$, $R^{31}$, and Ring A are respectively as defined hereinbefore; Y represents oxygen, sulfur, or $SO_2$)

A compound of general formula [IV] is treated with an acid or heated for aromatization and, where necessary, the protective group is removed to provide compound [I]. This reaction can be carried out by a known method (J. Chem. Soc. C., 1971, 1227).

Process 3

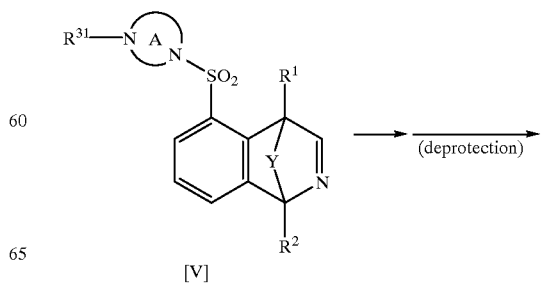

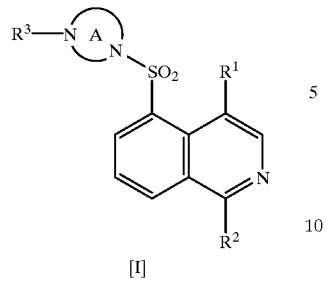

[I]

(wherein $R^1$, $R^2$, $R^3$, $R^{31}$, Ring A, and Y are respectively as defined hereinbefore)

A compound of general formula [V] is treated with an acid or heated for aromatization and, where necessary, the protective group is removed to provide compound [I]. This reaction can be carried out by a known method (J. Chem. Soc. C., 1971, 1227).

Process 4

Compound of formula [I] wherein $R^2$ is hydrogen and $R^1$ is a group other than halogen

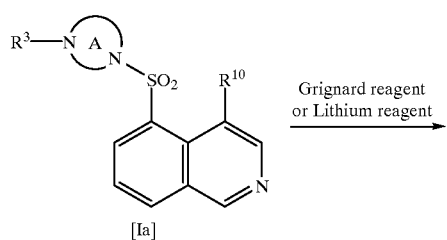

[Ia]

Grignard reagent or Lithium reagent

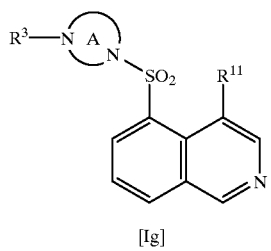

[Ig]

(wherein $R^3$ and Ring A are as defined hereinbefore; $R^{11}$ represents a group other than halogen among the species mentioned for $R^1$; $R^{10}$ represents halogen)

The halogen for $R^{10}$ is preferably chlorine or bromine.

A halide of general formula [Ia] is treated with an organometallic reagent corresponding to $R^{11}$ such as a Grignard reagent or alkyllithium; an alkali such as an alkali metal hydroxide (e.g. sodium hydroxide and potassium hydroxide) or a sodium alkoxide (e.g. sodium methoxide and sodium ethoxide); or potassium cyanide to provide compound [Ig] (compound of formula [I] wherein $R^2$ is hydrogen and $R^1$ is a substituent other than halogen). This reaction can be carried out by a known method (EP-A-429,341).

Compound [Ib] wherein Ring A represents a non-bridged cyclic amino group can be produced by the following method as well.

Process 5

(formula [I] wherein Ring A is a non-bridged cyclic amino group)

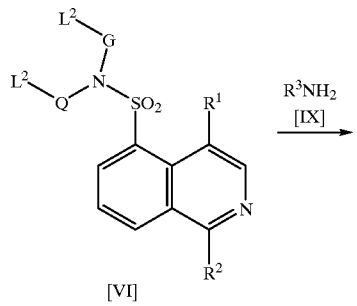

[VI]

$R^3NH_2$ [IX]

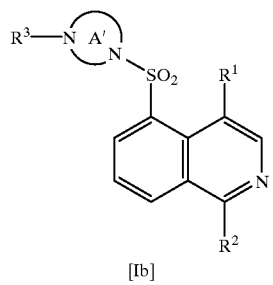

[Ib]

(wherein $R^1$, $R^2$, and $R^3$ are as defined hereinbefore; G represents $C_{2-5}$ alkylene and Q represents $C_{1-4}$ alkylene; which alkylene groups may respectively have 1 to 4 same or different substituent(s) selected from among the substituents mentioned for Ring A in any substitutable positions; the cyclic group

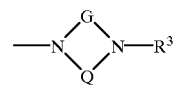

which forms upon reaction of compound [VI] with compound [IX] represents

wherein ring A' represents a non-bridged cyclic amino group; $L^2$ represents a leaving group).

The leaving group $L^2$ includes halogen such as chlorine or bromine and acyloxy such as acetyloxy, mesyloxy or tosyloxy.

Compound [VI] (a halide or a reactive derivative) is reacted with compound [IX] (the amine, guanidine or ammonia corresponding to $R^3$) to provide compound [Ib]. This reaction can be carried out by a known method (Acta. Chemica. Scand., 1991, 45, 621).

Process 6

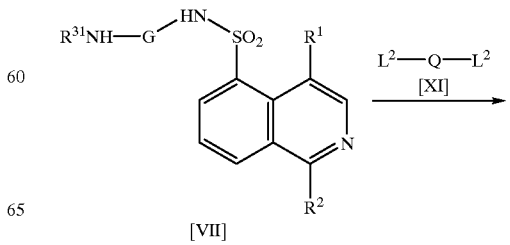

[VII]

$L^2$—Q—$L^2$ [XI]

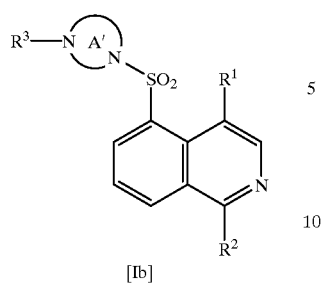

[Ib]

(wherein $R^1$, $R^2$, $R^3$, $R^{31}$, $L^2$, G, and Q are respectively as defined hereinbefore)

Compound [XI] (a halide or reactive derivative) is reacted with compound [VII] and, where necessary, the protective group is removed with an acid or an alkali to provide compound [Ib]. This reaction can be carried out by a known method (Acta. Chemica. Scand., 1991, 45, 621).

Process 7

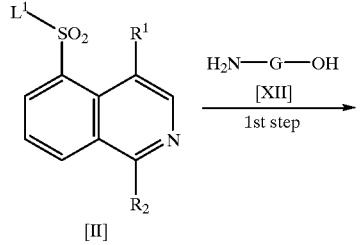

[II]

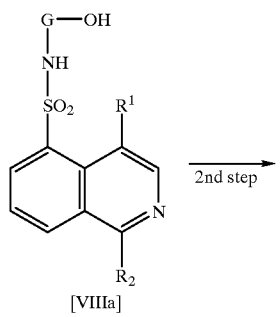

[VIIIa]

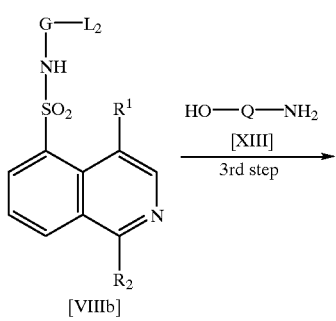

[VIIIb]

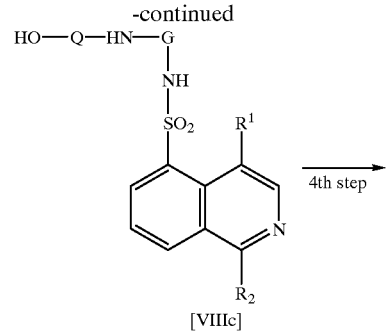

[VIIIc]

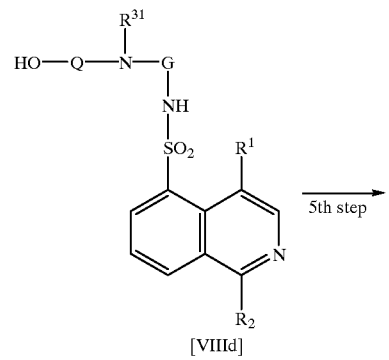

[VIIId]

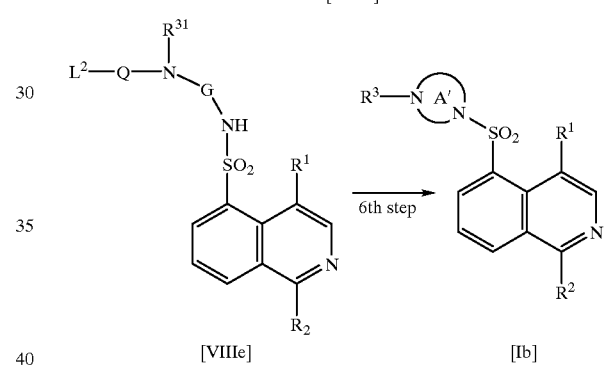

[VIIIe]                [Ib]

(wherein $R^1$, $R^2$, $R^3$, $R^{31}$, Ring A', G, Q, $L^1$, and $L^2$ are respectively as defined hereinbefore)

Step 1 Aminoalkyl alcohol of formula [XII] is reacted with compound [II] as in Process 1 to provide compound [VIIIa].

Step 2 By a per se known procedure, the hydroxyl group of compound [VIIIa] is converted to halogen (e.g. Cl, Br) or acyloxy (e.g. tosyloxy, methanesulfonyloxy, acetyloxy) to provide compound [VIIIb].

Step 3 Compound [VIIIb] is reacted with aminoalkyl alcohol [XIII] in a suitable solvent, either in the absence or in the presence of a base, in otherwise the same manner as Process 1 to provide compound [VIIIc].

Step 4 The secondary amino group of compound [VIIIc] is protected by a per se known procedure to provide compound [VIIId]. The protective group may be any of the protective groups mentioned for Process 1.

Step 5 In the routine manner, compound [VIIId] is converted to compound [VIIIe].

Step 6 Compound [VIIIe] is treated with a base in a suitable solvent and, where necessary, further treated with an acid or an alkali to remove the protective group, whereby compound [Ib] is obtained. The base which can be used includes various alkalies such as sodium hydride, sodium hydrogencarbonate, potassium carbonate, sodium hydroxide and potassium hydroxide and organic tertiary amines such as triethylamine and triethylenediamine. This reaction is carried out using the same reaction solvent under the same conditions as mentioned for Process 1.

Compound [Ib] can also be obtained by subjecting compound [VIIId] to intramolecular dehydration reaction using triphenylphosphine and diethyl azodicarboxylate and removing the protective group.

The compound of formula [I] wherein $R^1$ is alkenyl or $C_{2-6}$ alkyl can also be produced by reducing the compound [Ic] (formula [I] in which $R^1$ is alkynyl) prepared by any of the above-described processes. For example, the compound [I] wherein $R^1$ is alkenyl can be obtained by subjecting compound [Ic] to catalytic reduction in a solvent such as methanol, ethanol, ethyl acetate, or quinoline in the presence of palladium/barium carbonate, palladium/calcium carbonate, or Rindlar catalyst at atmospheric temperature and pressure. The compound in which $R^1$ is alkyl can be obtained by subjecting the compound in which $R^1$ is alkynyl or alkenyl to catalytic reduction with the aid of a catalyst such as platinum, platinum oxide, palladium-on-carbon, or Raney nickel in a solvent such as methanol, ethanol, or acetic acid at atmospheric temperature and pressure or optionally at elevated temperature and pressure.

The compound of formula [I] in which $R^1$ is alkyl and $R^2$ is hydroxy or halogen can also be produced by oxidizing the compound [Id] (formula [I] in which $R^1$ is alkyl and $R^2$ is hydrogen) obtained by any of the above-described processes. Thus, the compound in which $R^2$ is hydroxy can be obtained by heating compound [Id] together with an oxidizing agent such as hydrogen peroxide, a peracid, or tert-butyl peroxide in a solvent such as acetic acid, methylene chloride, or chloroform to give isoquinoline N-oxide and hydrolyzing the same with acetic anhydride under heating. Furthermore, by heating said isoquinoline N-oxide together with phosphorus oxychloride or phosphorus tribromide, the compound in which $R^2$ is halogen can be provided.

The compound [I] having a substituent on the nitrogen atom of Ring A, i.e. compound [Ie] ($R^3$ in formula [I] represents alkyl or amidino), can also be produced by introducing a substituent group into the compound [If] ($R^3$ in formula [I] represents hydrogen) obtained by any of the processes described hereinbefore. For example, the compound having alkyl for $R^3$ can be obtained by reacting compound [If] with an alkylating agent in the presence of a base. The compound having amidino for $R^3$ can be obtained by reacting compound [If] with an isourea derivative in the presence of a base. The base which can be used here includes various alkalies such as sodium hydrogencarbonate, potassium carbonate, sodium hydroxide and potassium hydroxide, and organic tertiary amines such as triethylamine and so forth. The reaction solvent which can be used includes but is not limited to ethanol, methanol, benzene, toluene, N,N-dimethylformamide, and dimethyl sulfoxide. Thus, the compound in which $R^3$ is amidino can be produced by reacting compound [If] with S-methylisothiourea or O-methylisourea in a solvent (e.g. tetrahydrofuran, ethanol, or methanol) at room temperature or under heating.

In the above production processes, hydroxyl and amino groups can be protected, whenever necessary, with suitable known protective groups and, after completion of the contemplated reaction, deprotected by per se known procedures such as acid treatment, alkali treatment, and catalytic reduction. The amino-protecting group that can be used includes but is not limited to benzyl, benzyloxycarbonyl, and trifluoroacetyl. The hydroxy-protecting group that can be used includes but is not limited to methoxymethyl, 2-methoxyethoxymethyl, methylthiomethyl, tetrahydropyranyl, tert-butyl, benzyl, trimethylsilyl, and tert-butyldimethylsilyl. When the hydroxyl group is protected with benzyl, the catalytic reduction results in simultaneous debenzylation to regenerate a free hydroxyl group.

The starting compound [II] can be prepared by the procedure described in Reference Example 1.

The starting compound [III] can be purchased from a commercial source or prepared by the procedure described in Reference Example 2.

The starting compounds [IV] and [V] can be prepared by the method described in J. Chem. Soc. C., 1971, 1227.

The starting compounds [VI] and [VII] can be prepared in accordance with the procedures described in Acta. Chemica. Scand., 1991, 45, 621.

The starting compounds [IX] and [XI] can be purchased from commercial sources.

The starting compounds [XII] and [XIII] can also be purchased from commercial sources.

While compound [I] wherein $R^2$ represents hydroxy may exist in the following tautomeric forms, both isomers fall within the scope of the invention.

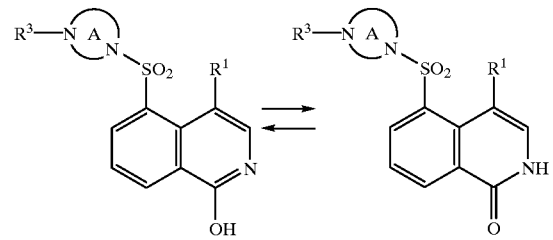

Some species of the compound [I] of the invention have asymmetric carbon atoms and, as such, each may occur as optical isomers. Such respective isomers and mixtures thereof also fall within the scope of the invention. Usually, a racemic modification is produced. While the racemic modification as such is pharmacologically active, each racemic modification may optionally be resolved into the component isomers. Such a mixture of isomers can be fractionated into the respective isomers by known optical resolution techniques, for example the technique which comprises reacting the racemic modification with an optically active carboxylic acid (e.g. (+)- or (−)-tartaric acid or (+)- or (−)-malic acid) or sulfonic acid (e.g. (+)-camphorsulfonic acid) to provide a salt and isolating the salt by fractional crystallization or the technique which comprises using a chiral column. Optical isomers can be also obtained by using the optically active form of starting compound [III], [IV], [V], [VI], [VII], [XII], [XIII], or [Ia] (S-configuration or R-configuration).

The salt of compound [I] of the present invention can be provided by a per se known method. For example, the hydrochloride of compound [I] can be prepared by dissolving compound [I] in a solution of hydrogen chloride in alcohol or ethyl ether.

Recrystallizing compound [I] or a salt thereof from a suitable solvent (inclusive of water) may give rise to the corresponding solvate (inclusive of hydrate). Such solvates also fall within the scope of the invention. For example, the hydrate of compound [I] according to the invention may form upon recrystallization of compound [I] from an aqueous alcohol.

The compound of the invention may show polymorphism. Such polymorphs all fall within the scope of the invention.

The compound of the invention as produced in the above manner can be isolated and purified, in the form of a free base or an acid addition salt, by per se known procedures such as concentration, pH adjustment, redistribution, solvent extraction, crystallization, fractional distillation, and chromatography.

The compound of the invention has cerebral vasospasm-inhibiting activity and, as such, can be used with advantage in the prevention and treatment of cerebrovascular diseases, particularly brain tissue impairments due to the cerebral vasospasm following cerebral hemorrhage.

For use as a medicine, the compound of the invention can be administered either as it is or in the form of a medicinal composition containing it in a proportion of 0.1%–99.5%, preferably 0.5–90%, in a medicinally acceptable, nontoxic, and inert carrier, to mammalian animals inclusive of humans.

As the carrier mentioned above, one or more members selected from among solid, semi-solid, or liquid diluents, fillers, and other formulating additives can be used. The medicinal composition is preferably administered in unit dosage forms. The medicinal composition of the invention can be administered orally, parenterally, locally (e.g. transdermally), or rectally. Of course, a dosage form suited for each route of administration should be selected. Among the above-mentioned routes of administration, the intravenous and oral routes are particularly preferred.

The dosage is preferably adjusted according to patient factors such as age and body weight, the route of administration, and the nature and severity of illness. For use as a prophylactic or therapeutic drug for cerebral vasospasm in adult patients, the daily intravenous dose as the active compound may be 0.1–100 mg/patient, preferably 1–30 mg/patient. For oral administration, the daily dose may be 1–1,000 mg/patient, preferably 1–30 mg/patient. Lower doses may suffice in certain cases, while higher doses may be needed in other cases. Moreover, the above daily dosage may be administered in a few divided doses.

Oral administration can be carried out using a solid or liquid unit dosage form, for example, bulk powders, powders, tablets, dragees, capsules, granules, suspension, solution, syrup, drops, sublingual tablets, and so on.

Bulk powders can be produced by comminuting the compound of the invention to a suitable particle diameter. Powders can be manufactured by comminuting the compound to a suitable particle diameter and mixing the resulting powder with a pharmaceutical carrier, for example an edible carbohydrate such as starch or mannitol, which has also be similarly comminuted beforehand. Where necessary, the resulting powders may be further supplemented with a flavorant, preservative, dispersant, coloring agent, perfume, and/or other additives.

Capsules can be manufactured by filling gelatin or other capsule shells with said bulk powders or the powders prepared as above, or the granules prepared by the procedure described below for tablets. Lubricants and/or fluidizing agents, such as colloidal silica, talc, magnesium stearate, calcium stearate, and solid polyethylene glycol, may be added in finely divided form prior to the filing operation described above. Disintegrators and solubilizers, such as carboxymethylcellulose, carboxymethylcellulose calcium, low-substitution hydroxypropylcellulose, croscarmellose sodium, carboxymethylstarch sodium, calcium carbonate, and sodium carbonate can also be added, in which case the efficacy of the drug after ingestion of the capsules may be enhanced.

The finely divided compound of the invention can be suspended and dispersed in vegetable oil, polyethylene glycol, glycerin, or a surfactant and packaged in gelatin sheets to provide soft capsules. Tablets can be manufactured by preparing a powdery mixture of the compound with an excipient, processing it into granules or slags, adding a disintegrator and/or a lubricant, and compressing the mixture. The powdery mixture can be prepared by mixing adequately pulverized powders of the active compound with any of said diluents or bases. Where necessary, binders (e.g. carboxymethylcellulose sodium, methylcellulose, hydroxypropylmethylcellulose, gelatin, polyvinylpyrrolidone, polyvinyl alcohol, etc.), dissolution retardants (e.g. paraffin), reabsorption agents (e.g. quaternary salts), and/or adsorbents (e.g. bentonite, kaolin, dicalcium phosphate, etc.) can also be added. The powdery mixture can be made into granules by wetting it with a binder, such as a syrup, a starch paste, gum arabic, a cellulose solution, or a polymer solution, stirring the wet powder well, drying it, and pulverizing the same. Instead of converting the powders to granules in the above manner, the powders may be compressed with a tablet machine and the resulting crude slags be comminuted into granules. The granules thus prepared can be protected against conglomeration by adding a lubricant such as stearic acid, a salt of stearic acid, talc or mineral oil. The thus-lubricated composition is then compressed. The resulting core tablets can be coated with a film coating agent or a sugar coating agent.

As an alternative, the active compound can be directly mixed with a free-flowing inert carrier without being subjected to the above-mentioned granulation or slagging procedure and the mixture be directly compressed. A transparent or translucent protective coating capable of yielding a hermetic shellac or other film, a sugar coating, a polymer coating, or a glaze wax coating, for instance, can also be applied. Other dosage forms for oral administration, such as solutions, syrups, and elixirs, can also be provided in unit dosage forms each containing a predetermined amount of the drug. Syrups are manufactured by dissolving the active compound in a suitable flavored aqueous medium, while elixirs are manufactured using a nontoxic alcoholic vehicle. Suspensions are prepared by dispersing the active compound in nontoxic vehicles. Where necessary, solubilizers and emulsifiers (e.g. ethoxylated isostearyl alcohol, polyoxyethylene sorbitol ester, etc.) as well as preservatives and flavorants (e.g. peppermint oil, saccharin, etc.) can also be added.

If necessary, unit dosage formulations for oral administration can be microencapsulated. Such formulations can also be coated with, or embedded in, a polymer or wax matrix for prolonged action or sustained release.

Parenteral administration can be carried out using liquid unit dosage forms, e.g. solutions or suspensions, for subcutaneous, intramuscular or intravenous injection. Such dosage forms can be manufactured by suspending or dissolving a predetermined amount of the active compound in an injectable nontoxic liquid vehicle, e.g. an aqueous medium or an oily medium, and sterilizing the resulting suspension or solution. To make an injection isotonic, a nontoxic salt or a solution thereof can be added. Moreover, stabilizers, preservatives, emulsifiers, and other additives can also be employed.

Rectal administration can be made using suppositories manufactured by dissolving or suspending the active compound in a low-melting water-soluble or water-insoluble solid medium, e.g. polyethylene glycol, cacao butter, a semi-synthetic oleaginous base (e.g. Witepsol™), a higher fatty acid ester (e.g. myristyl palmitate) or a mixture thereof.

BEST MODE FOR CARRYING OUT THE INVENTION

The following reference examples relating to the production of representative starting compounds, working examples concerning the production of the compound of the invention, and formulation and test examples for and using representative species of the compound of the invention are all intended to illustrate the present invention in further detail and should by no means be construed as defining the scope of the invention. It should be understood that the specific rotation was measured at 20° C.

Reference Example 1

5-Chlorosulfonyl-4-methylisoquinoline
(1) 4-Methyl-5-nitroisoquinoline

To 45 ml of concentrated sulfuric acid was added 12.75 g of 4-methylisoquinoline (produced according to Tetrahedron, 1982, 38, 3347) under ice-cooling, and a solution of 9.02 g of potassium nitrate in 34 ml of concentrated sulfuric acid was added dropwise at a temperature not exceeding 0° C. After 30 minutes of stirring, the reaction mixture was poured in iced water containing aqueous ammonia and extracted with ethyl acetate. The extract was dried over anhydrous magnesium sulfate and the solvent was distilled off under reduced pressure. The residue was purified by silica gel column chromatography (hexane/ethyl acetate=1/1) to provide 12.0 g of light-yellow crystals.
(2) 5-Amino-4-methylisoquinoline To 120 ml of a solution prepared by dissolving 12.0 g of 4-methyl-5-nitroisoquinoline obtained in (1) in methanol was added 0.73 g of platinum oxide, and catalytic reduction was carried out at 25° C. for 2 hours in a hydrogen stream at 1 atmospheric pressure. This reaction mixture was filtered and the filtrate was concentrated. The residue was purified by silica gel column chromatography (chloroform/acetone=9/1) to provide 9.12 g of light-brown crystals.
(3) 5-Chlorosulfonyl-4-methylisoquinoline To a suspension of 11.5 g of 5-amino-4-methylisoquinoline obtained in the same manner as (2) in concentrated hydrochloric acid was added 36 ml of an aqueous solution of 7.2 g of sodium nitrite dropwise at −5° C. and the mixture was stirred for 1 hour. This reaction mixture was added dropwise to a mixture of 200 ml of sulfur dioxide gas-saturated acetic acid and 4.1 g of cupric chloride hydrate at room temperature. After 1 hour of stirring, the reaction mixture was concentrated, made basic with sodium hydrogencarbonate, and extracted with chloroform. The extract was dried and concentrated and the resulting crude crystals were recrystallized from benzene to provide 8.1 g of the objective compound (light-yellow crystals).
m.p. 113–118° C.

Reference Example 2

(S)-Hexahydro-2-methyl-1H-1,4-diazepine hydrobromide
(1) (S)-3-[N-(t-Butoxycarbonyl)-N-[2-(N-p-toluene-sulfonyl)aminopropyl]amino]-1-propanol L-Alaninol was N,O-ditosylated in the routine manner and the O-tosyl moiety of the resulting compound was subjected to a substitution reaction with 3-amino-1-propanol. Thus, 17.7 g of tosyl chloride was added to a solution of 3.2 g of L-alaninol in 50 ml of pyridine under ice-cooling and the mixture was stirred at room temperature for 3 days. This reaction mixture was concentrated and the residue was diluted with ether, washed with 1N-hydrochloric acid and water, dried, and concentrated. The residue was dissolved in 150 ml of tetrahydrofuran, 3-aminopropanol was added under ice-cooling, and the mixture was stirred at room temperature for 1.5 hours. The reaction mixture was then concentrated and chloroform was added to the residue. This mixture was washed with saturated aqueous sodium hydrogencarbonate solution and saturated aqueous sodium chloride solution, dried, and concentrated. The residue was purified by silica gel column chromatography (methylene chloride/methanol/aqueous ammonia=8:1:0.1) to provide 10.2 g of (S)-3-[N-[2-[N-[(p-toluene)sulfonyl]amino]propyl]-amino]-1-propanol (brown oil). This compound, 10.2 g, was dissolved in 90 ml of dioxane-water (2:1) and, under ice-cooling, 50 ml of 1N aqueous sodium hydroxide solution and 11.6 g of di-tert-butyl dicarbonate were added, followed by stirring at room temperature overnight. This reaction mixture was concentrated, diluted with chloroform and water, neutralized with 5% aqueous potassium hydrogensulfate, and extracted with chloroform. The extract was dried and filtered and the filtrate was distilled under reduced pressure to provide 13.7 g of (S)-3-[N-(tert-butoxycarbonyl)-N-[2-[N-[(p-toluene)sulfonyl]amino]propyl]amino]-1-propanol (light-yellow oil). This oil was submitted to the next reaction without purification.
(2) (S)-(−)-Hexahydro-2-methyl-1H-1,4-diazepine hydrobromide To a tetrahydrofuran solution of 13.7 g of the compound obtained in (1), triphenylphosphine and diethyl azodicarboxylate (40% in toluene) were added in bolus and the mixture was stirred under dryer heating for 20 minutes. This reaction mixture was concentrated and the residue was purified by silica gel column chromatography (n-hexane/ethyl acetate=3/1) to provide 13.1 g of colorless oil. This oil was dissolved in 180 ml of 30% hydrogen bromide/acetic acid and the mixture was stirred at room temperature for 30 minutes. Then, 13.4 g of phenol was added and the mixture was further stirred for 7 hours at 60° C. This reaction mixture was concentrated, a small amount of ethanol was added to the residue, and the resulting crystal crop was harvested by filtration and dried to provide 6.44 g of (S)-(−)-hexahydro-2-methyl-1H-1,4-diazepine hydrobromide (white crystals).

$[\alpha]_D$: −13.60° (c=1.12, $H_2O$)

Reference Example 3

2,7-Dimethyl-hexahydro-1H-1,4-diazepine hydrobromide

Using 3-aminobutan-1-ol in lieu of D-alaninol, the procedure of Reference Example 2 was otherwise repeated to provide the title compound.

EXAMPLE 1

Hexahydro-1-[(4-methyl-5-isoquinolinyl)sulfonyl]-1H-1,4-diazepine dihydrochloride
(1) To 30 ml of a solution prepared by dissolving 1 g of 1-(tert-butoxycarbonyl)hexahydro-1H-1,4-diazepine and 0.97 g of triethylamine in chloroform was added 1 g of 5-chlorosulfonyl-4-methylisoquinoline under ice-cooling, and the mixture was stirred for 18 hours. This reaction mixture was poured in iced water and extracted with chloroform. The extract was dried and concentrated and the resulting oil was purified by silica gel column chromatography to provide 1.38 g of oil. This oil was dissolved in 30 ml of ethanol, and after 20 ml of 1N-hydrochloric acid was added, the mixture was refluxed for 1 hour. This reaction mixture was concentrated and the residue was made basic and extracted with chloroform. After drying, the solvent was distilled off to provide 0.72 g of white crystals.
(2) The above crystals were dissolved in chloroform, and hydrogen chloride-saturated ethanol was added thereto. The mixture was concentrated and the resulting white crystals were harvested to provide the objective compound (0.8 g).

Elemental analysis (for $C_{15}H_{19}N_3O_2.2HCl.H_2O$) Calcd. (%): C, 45.42; H, 5.80; N, 10.61 Found (%): C, 45.82; H, 5.69; N, 10.56 IR spectrum (KBr): ν (cm$^{-1}$) 3300, 1639, 1615, 1472, 1333, 1146, 764

EXAMPLE 2

1-[(4-Bromo-5-isoquinolinyl)sulfonyl]piperazine dihydrochloride

To a solution prepared by dissolving 0.56 g of piperazine and 0.66 g of triethylamine in chloroform was added 1.0 g of (4-bromo-5-chlorosulfonyl)isoquinoline (synthesized in accordance with Japanese Kokai Tokkyo Koho H2-67274) under ice-cooling. The mixture was stirred at room temperature for 2 hours, after which it was concentrated. The residue was purified by silica gel column chromatography (chloroform/methanol=9/1) and further treated as in Example 1 (2) to provide 0.45 g of the objective compound (white crystals).

m.p. 230–235° C.

Elemental analysis (for $C_{13}H_{14}BrN_3O_2S.2HCl.1/2H_2O$) Calcd. (%): C, 35.62; H, 3.87; N, 9.59 Found (%): C, 35.38; H, 3.63; N, 9.45

EXAMPLE 3

1-[(4-Ethynyl-5-isoquinolinyl)sulfonyl]hexahydro-1H-1,4-diazepine dihydrochloride (1) To 30 ml of a solution prepared by dissolving 2.72 g of 1-(tert-butoxycarbonyl)hexahydro-1H-1,4-diazepine and 2.74 g of triethylamine in chloroform was added 4.17 g of (4-bromo-5-chlorosulfonyl)isoquinoline under ice-cooling, and the mixture was stirred at room temperature for 12 hours and then concentrated. The residue was purified by silica gel column chromatography (chloroform/acetone=19/1) to provide 4.51 g of 1-(tert-butoxycarbonyl)-4-[(4-bromo-5-isoquinolinyl)sulfonyl]hexahydro-1H-1,4-diazepine as white crystals.

(2) To a suspension prepared by suspending 2.72 g of the above compound, 0.12 g of dichlorobis(triphenylphosphine) palladium, and 0.06 g of copper iodide in 5 ml of triethylamine was added 1.14 g of trimethylsilylacetylene, and the mixture was stirred in a sealed tube at 80° C. for 12 hours. This reaction mixture was filtered and the filtrate was extracted with ethyl acetate. The extract was dried and concentrated and the residue was purified by silica gel column chromatography (chloroform/acetone=9/1). The crystals obtained were dissolved in methanol and followed by the addition of 20 ml of 1N-potassium hydroxide/$H_2O$, the solution was stirred at room temperature for 5 minutes. This reaction mixture was diluted with water, extracted, dried, and concentrated to provide 2.06 g of 1-(tert-butoxycarbonyl)-4-[(4-ethynyl-5-isoquinolinyl)]hexahydro-1H-1,4-diazepine.

(3) To a solution prepared by dissolving 0.24 g of the above compound in chloroform was added 2 ml of trifluoroacetic acid under ice-cooling, and the mixture was stirred at room temperature for 1 hour. This reaction mixture was poured in iced water, made basic with 2N-sodium hydroxide/$H_2O$, and extracted with chloroform. The extract was dried and concentrated and the residue was further treated as in Example 1 (2) to provide 0.16 g of the objective compound as white crystals.

m.p. 190–196° C.

Elemental analysis (for $C_{16}H_{17}N_3O_2S.2HCl.2H_2O$) Calcd. (%): C, 45.29; H, 5.46; N, 9.90 Found (%): C, 45.61; H, 5.82; N, 9.49

EXAMPLE 4

1-[(4-Ethenyl-5-isoquinolinyl)sulfonyl]hexahydro-1H-1,4-diazepine dihydrochloride To 30 ml of a solution prepared by dissolving 0.62 g of 1-(tert-butoxycarbonyl)-4-[(4-ethynyl-5-isoquinolinyl)]hexahydro-1H-1,4-diazepine obtained in Example 3 (2) in methanol was added 0.062 g of platinum oxide and catalytic reduction was carried out in a hydrogen stream for 25 minutes. This reaction mixture was filtered and the filtrate was concentrated. The residue was purified by silica gel column chromatography (chloroform/acetone=9/1). To a solution of the crystal crop thus obtained in ethanol was added 1N-hydrochloric acid and the mixture was refluxed for 3 hours. The reaction mixture was then concentrated, made basic with 2N-sodium hydroxide/$H_2O$, and extracted with chloroform. The extract was dried and concentrated and the residue was purified by silica gel column chromatography (chloroform/methanol=9/1) and further treated as in Example 1 (2) to provide 0.14 g of the objective compound (white crystals).

m.p. 210–215° C.

Elemental analysis (for $C_{16}H_{19}N_3O_2S.2HCl.H_2O$) Calcd. (%): C, 47.02; H, 5.63; N, 10.29 Found (%): C, 46.98; H, 5.90; N, 10.24

EXAMPLE 5

1-[(4-Ethyl-5-isoquinolinyl)sulfonyl]hexahydro-1H-1,4-diazepine dihydrochloride

Using 0.25 g of 1-(tert-butoxycarbonyl)-4-[(4-ethynyl-5-isoquinolinyl)]hexahydro-1H-1,4-diazepine, catalytic reduction was carried out for 10 hours and the reaction mixture after-treated as in Example 4 to provide 0.082 g of the objective compound as white crystals.

Elemental analysis (for $C_{16}H_{21}N_3O_2S.2HCl.H_2O$) Calcd. (%): C, 46.80; H, 6.09; N, 10.24 Found (%): C, 46.50; H, 5.75; N, 10.47 IR spectrum (KBr): ν (cm$^{-1}$) 3400, 1644, 1615, 1468, 1335, 1144, 1011, 589

EXAMPLE 6

Hexahydro-4-[(4-methyl-5-isoquinolinyl)sulfonyl]-1H-1,4-diazepine-1-carboximidamide dihydrochloride S-Methylisothiourea sulfate was benzyloxycarbonylated in the routine manner (Jikken Kagaku Koza [Experimental Chemistry Series] 22, Yuki Gosei (Organic Synthesis), Edition IV, 1992, 228) and then reacted with 4 molar equivalents of homopiperazine in tetra-hydrofuran to prepare hexahydro-1H-1,4-diazepine-1-carboximidamide. Using 0.68 g of this compound and 0.5 g of 5-chlorosulfonyl-4-methylisoquinoline, the reaction procedure of Example 1 was otherwise repeated to provide 0.16 g of the objective compound as white crystals.

Elemental analysis (for $C_{16}H_{21}N_5O_2S.2HCl.2H_2O$) Calcd. (%): C, 42.07; H, 5.92; N, 15.34 Found (%): C, 42.73; H, 5.46; N, 15.27 IR spectrum (KBr): ν (cm$^{-1}$) 3300, 1653, 1607, 1327, 1148, 569

EXAMPLE 7

Hexahydro-1-[(1-hydroxy-4-methyl-5-isoquinolinyl) sulfonyl]-1H-1,4-diazepine hydrochloride To 30 ml of a suspension prepared by suspending 2.25 g of hexahydro-1-[(4-methyl-5-isoquinolinyl)sulfonyl]-1H-1, 4-diazepine in pyridine was added 2.0 g of acetic anhydride, and the mixture was stirred at 60° C. for 30 minutes. This reaction mixture was concentrated, made basic with sodium hydrogencarbonate/$H_2O$, and extracted with chloroform. The extract was dried and concentrated to provide 1.91 g of 1-acetyl-hexahydro-4-[(4-methyl-5-isoquinolinyl)sulfonyl]-1H-1,4-diazepine as oil.

In 30 ml of acetic acid was dissolved 1.91 g of the above compound, followed by addition of 0.94 g of 30% hydrogen peroxide/$H_2O$ at room temperature, and the mixture was stirred at 70° C. for 16 hours. This reaction mixture was poured in water and made basic with potassium carbonate and the resulting crystal crop was harvested by filtration to provide 1.87 g of 5-(4-acetyl-hexahydro-1H-1,4-diazepin-1-yl)sulfonyl-4-methylisoquinoline-2-oxide as white crystals.

A solution prepared by dissolving 1.87 g of the above compound in 40 ml of acetic anhydride was refluxed for 4 hours and then concentrated. The residue was dissolved in 20 ml of methanol, and after addition of 10 ml of 2N-sodium hydroxide/$H_2O$, the mixture was stirred at 60° C. for 5 minutes. The reaction mixture was poured in water, acidified with 1N-hydrochloric acid, and extracted with chloroform. The extract was dried and concentrated and the residue was purified by silica gel column chromatography (chloroform/methanol=17/1) to provide 1.15 g of 1-acetyl-hexahydro-4-[(1-hydroxy-4-methyl-5-isoquinolinyl)sulfonyl]-1H-1,4-diazepine. A suspension of this compound in 1N-hydrochloric acid was refluxed for 11 hours and then concentrated. The residue was purified by silica gel column chromatography (chloroform/methanol=4/1) and treated as in Example 1 (1) to provide 0.487 g of the objective compound as white crystals.

Elemental analysis (for $C_{15}H_{19}N_3O_3S \cdot HCl$) Calcd. (%): C, 50.34; H. 5.63; N, 11.74 Found (%): C, 49.80; H, 5.57; N, 11.37 IR spectrum (KBr): ν ($cm^{-1}$) 1636, 1593, 1323, 1146, 1011, 762, 596

EXAMPLE 8

Hexahydro-1-[[4-(1-propynyl)-5-isoquinolinyl]-sulfonyl]-1H-1,4-diazepine hydrochloride Using 0.24 g of 1-(trimethylsilyl)-1-propyne and 0.55 g of 1-(tert-butoxycarbonyl)-4-[(4-bromo-5-isoquinolyl)sulfonyl]hexahydro-1H-1,4-diazepine, the procedure of Example 3 was otherwise repeated to provide 0.23 g of the objective compound (white crystals).

m.p. 250° C. (decomp.)

Elemental analysis (for $C_{17}H_{19}N_3O_2S \cdot HCl \cdot 1/2H_2O$) Calcd. (%): C, 54.40; H, 5.60; N, 11.20 Found (%): C, 54.29; H, 5.60; N, 11.28

EXAMPLE 9

3-[(4-Methyl-5-isoquinolinyl)sulfonyl]-3,6-diazabicyclo[3.2.2]nonane hydrochloride To a solution prepared by dissolving 0.4 g of 3-benzyl-6-ethoxycarbonyl-3,6-diazabicyclo[3.2.2]nonane (synthesized in accordance with Japanese Kokai Tokkyo Koho S64-16783, Example 2) in 10 ml of acetic acid was added 0.4 g of platinum oxide, and hydrogenation reaction was carried out under a pressure of 4 atmospheres for 15 hours, followed by filtration. The filtrate was concentrated, made basic with sodium hydrogencarbonate/$H_2O$, and extracted with chloroform. The extract was dried and concentrated to provide 0.2 g of 6-ethoxycarbonyl-3,6-diazabicyclo[3.2.2]nonane. This compound was further reacted with 0.336 g of 5-chlorosulfonyl-4-methylisoquinoline in the same manner as in Example 1 (1) to provide 0.5 g of 6-ethoxycarbonyl-3-[(4-methyl-5-isoquinolinyl)sulfonyl]-3,6-diazabicyclo[3.2.2]nonane (pale yellow crystals). This compound was added to 30% hydrogen bromide/acetic acid and the mixture was refluxed for 6 hours. This reaction mixture was concentrated and the residue was made basic with 10% sodium hydroxide/$H_2O$ and extracted with chloroform. The extract was dried and concentrated and the residue was purified by silica gel column chromatography (chloroform/methanol/aqueous ammonia=90/10/1) and further treated as in Example 1 (2) to provide 0.3 g of the objective hydrochloride (pale brown crystals).

Elemental analysis (for $C_{17}H_{21}N_3O_2S \cdot HCl \cdot H_2O$) Calcd. (%): C, 52.91; H, 6.27; N, 10.89 Found (%): C, 52.95; H, 6.01; N, 10.72 IR spectrum (KBr): ν ($cm^{-1}$) 3480, 3350, 1641, 1610, 1309, 1149, 1034, 765, 652

EXAMPLE 10

6-[(4-Methyl-5-isoquinolinyl)sulfonyl]-3,6-diazabicyclo[3.2.2]nonane hydrochloride In accordance with the procedure described in Example 1, 0.35 g of 3-(tert-butoxycarbonyl)-3,6-diazabicyclo[3.2.2]nonane (synthesized in accordance with Japanese Kokai Tokkyo Koho S64-16783) was reacted with 0.374 g of 5-chlorosulfonyl-4-methylisoquinoline and the reaction mixture was deprotected with trifluoroacetic acid and converted to the hydrochloride to provide 0.4 g of the objective compound (pale brown crystals).

Elemental analysis (for $C_{17}H_{21}N_3O_2S \cdot HCl \cdot H_2O$) Calcd. (%): C, 52.91; H, 6.27; N, 10.89 Found (%): C, 53.23; H. 6.15; N, 10.76 IR spectrum (KBr): ν ($cm^{-1}$) 3480, 3350, 1641, 1610, 1309, 1151, 1034, 765, 652

EXAMPLE 11

6-[(4-Methyl-5-isoquinolinyl)sulfonyl]-6,8-diazabicyclo[3.2.2]nonane dihydrochloride Using 3.34 g of 6,8-diazabicyclo[3.2.2]nonane (synthesized in accordance with J. Med. Chem., 1991, 34, 662), the procedure of Example 1 was otherwise repeated to provide 0.2 g of the objective compound (pale brown crystals).

m.p. 249–253° C.

Elemental analysis (for $C_{17}H_{21}N_3O_2S \cdot 2HCl \cdot 2H_2O$) Calcd. (%): C, 46.36; H, 7.17; N, 9.54 Found (%): C, 46.72; H, 7.22; N, 9.14

EXAMPLE 12

(S)-(+)-Hexahydro-2-methyl-1-[(4-methyl-5-isoquinolinyl)sulfonyl]-1H-1,4-diazepine hydrochloride To a suspension prepared by suspending 24.0 g of (S)-hexahydro-2-methyl-1H-1,4-diazepine hydrobromide obtained in Reference Example 2 in 40 ml of tetrahydrofuran were added 1.16 g of sodium hydroxide and 20 ml of 0.1N-sodium hydroxide/$H_2O$ under ice-cooling. Then, 1.58 g of di-tert-butyl dicarbonate was added dropwise and the mixture was stirred at room temperature overnight. This reaction mixture was concentrated and extracted with chloroform. The extract was dried and concentrated and the residue was purified by silica gel column chromatography (chloroform/methanol=10/1) to provide 1.5 g of colorless oil. This product was further reacted with 2.50 g of 5-chlorosulfonyl-4-methylisoquinoline as in Example 1 to provide 0.53 g of the objective compound (white crystals).

m.p. 146–150° C.

Elemental analysis (for $C_{16}H_{21}N_3O_2S.HCl.H_2O$) Calcd. (%): C, 51.40; H, 6.47; N, 11.24 Found (%): C, 51.40; H, 6.68; N, 11.26 $[\alpha]_D$: +16.05° (c=1.07, $H_2O$)

EXAMPLE 13

1-[(4-Bromo-5-isoquinolinyl)sulfonyl]-hexahydro-1H-1,4-diazepine dihydrochloride To a solution of 1.5 g of homopiperazine in methylene chloride were added triethylamine and 4-bromo-5-chlorosulfonylisoquinoline, and the mixture was stirred at room temperature and after-treated. The crude product was purified by silica gel column chromatography (chloroform/methanol=10/1) and further treated as in Example 1 to provide 0.55 g of the objective compound (white crystals).

m.p. 250–260° C. (decomp.)

Elemental analysis (for $C_{14}H_{16}BrN_3O_2S.2HCl$) Calcd. (%): C, 37.94; H, 3.64; N, 9.48 Found (%): C, 37.65; H, 3.94; N, 9.39

EXAMPLE 14

Hexahydro-1-[(4-methoxy-5-isoquinolinyl)sulfonyl]-1H-1,4-diazepine dihydrochloride In methanol was dissolved 0.35 g of sodium metal, followed by addition of 2.35 g of 1-(4-bromo-5-isoquinolinesulfonyl)homopiperazine and 60 mg of copper dust, and the mixture was refluxed for 48 hours. This reaction mixture was filtered with the aid of Celite and the filtrate was concentrated. The residue was diluted with iced water and chloroform. The chloroform layer was washed with water, dried over anhydrous magnesium sulfate, and concentrated. The oily residue, 0.3 g, was dissolved in methylene chloride. To this solution was added 3 ml of trifluoroacetic acid dropwise, and the mixture was stirred at room temperature for 2 hours. This reaction mixture was diluted with iced water, made weakly basic with potassium carbonate, and extracted with chloroform. The extract was dried and concentrated and the residue was purified by silica gel column chromatography (chloroform/methanol=30/1) and converted to the hydrochloride by the routine procedure to provide 0.1 g of the objective compound (white crystals).

m.p. 274–276° C. (decomp.)

Elemental analysis (for $C_{15}H_{19}N_3O_3S.2HCl$) Calcd. (%): C, 45.69; H, 5.37; N, 10.66 Found (%): C, 45.50; H, 5.27; N, 10.36

EXAMPLE 15

1-[(4-Fluoro-5-isoquinolinyl)sulfonyl]-hexahydro-1H-1,4-diazepine dihydrochloride Using 25 g of 4-bromoisoquinoline (synthesized in accordance with J. Am. Chem. Soc., 1942, 64, 783 and 1951, 73, 687), 4-fluoroisoquinoline was prepared. Using 5.87 g of this compound, 5-chlorosulfonyl-4-fluoroisoquinoline was synthesized by the same procedure as described in Reference Example 1. 1.0 g of the compound obtained was reacted with 1.6 g of 1-(tert-butoxycarbonyl)-hexahydro-1H-1,4-diazepine. The reaction mixture was after-treated in the same manner as in Example 1 to provide 1.40 g of the objective compound (white crystals).

m.p. 255–260° C. (decomp.)

Elemental analysis (for $C_{14}H_{16}FN_3O_2S.2HCl$) Calcd. (%): C, 43.99; H, 4.75; N, 10.99 Found (%): C, 43.72; H, 4.68; N, 10.85

EXAMPLE 16

1-[(4-Chloro-5-isoquinolinyl)sulfonyl]-hexahydro-1H-1,4-diazepine dihydrochloride Using 2.08 g of 4-chloroisoquinoline (synthesized in accordance with J. Org. Chem., 1961, 26, 468), 4-chloro-5-chlorosulfonylisoquinoline was synthesized as in Reference Example 1. Then, 1.30 g of this compound was reacted with 1.20 g of 1-(tert-butoxycarbonyl)-hexahydro-1H-1,4-diazepine and the reaction mixture was after-treated in the same manner as in Example 1 to provide 0.80 g of the objective compound (white crystals).

m.p. 251–253° C. (decomp.)

Elemental analysis (for $C_{14}H_{16}ClN_3O_2S.2HCl$) Calcd. (%): C, 42.17; H, 4.55; N, 10.54 Found (%): C, 42.19; H, 4.57; N, 10.24

EXAMPLE 17

3-Methyl-1-[(4-methyl-5-isoquinolinyl)sulfonyl]piperazine dihydrochloride

Using 0.60 g of 2-methylpiperazine and 0.49 g of 5-chlorosulfonyl-4-methylisoquinoline, the procedure of Example 1 was otherwise repeated to provide 0.47 g of the objective compound (white crystals).

m.p. 245–250° C. (decomp.)

Elemental analysis (for $C_{15}H_{19}N_3O_2S.2HCl$) Calcd. (%): C, 47.62; H, 5.59; N, 11.11 Found (%): C, 47.53; H, 5.27; N, 11.12

EXAMPLE 18

2-Methyl-1-[(4-methyl-5-isoquinolinyl)sulfonyl]piperazine dihydrochloride

Using 0.40 g of 1-(tert-butoxycarbonyl)-3-methylpiperazine and 0.49 g of 5-chlorosulfonyl-4-methylisoquinoline, the procedure of Example 1 was otherwise repeated to provide 0.3 g of the objective compound (white crystals).

m.p. 250–255° C. (decomp.)

Elemental analysis (for $C_{15}H_{19}N_3O_2S.2HCl$) Calcd. (%): C, 47.62; H, 5.59; N, 11.11 Found (%): C, 47.54; H, 5.81; N, 10.85

EXAMPLE 19

3,5-Dimethyl-1-[(4-methyl-5-isoquinolinyl)sulfonyl]piperazine dihydrochloride

Using 0.23 g of 2,6-dimethylpiperazine and 0.48 g of 5-chlorosulfonyl-4-methylisoquinoline, the procedure of Example 1 was otherwise repeated to provide 0.47 g of the objective compound (white crystals).

m.p. 266–274° C. (decomp.)

Elemental analysis (for $C_{16}H_{21}N_3O_2S.2HCl$) Calcd. (%): C, 48.98; H, 5.91; N, 10.71 Found (%): C, 48.89; H, 6.14; N, 10.67

EXAMPLE 20

Trans-2,5-Dimethyl-1-[(4-methyl-5-isoquinolinyl)sulfonyl]piperazine dihydrochloride Using 0.34 g of trans-1-(tert-butoxycarbonyl)-2,5-dimethylpiperazine and 0.64 g of 5-chlorosulfonyl-4- methylisoquinoline, the procedure of Example 1 was otherwise repeated to provide 0.43 g of the objective compound (white crystals).

m.p. 260–271° C. (decomp.)

Elemental analysis (for $C_{16}H_{21}N_3O_2S.2HCl$) Calcd. (%): C, 48.98; H, 5.91; N, 10.71 Found (%): C, 48.79; H, 6.03; N, 10.57

EXAMPLE 21

Hexahydro-7-methyl-1-[(4-methyl-5-isoquinolinyl) sulfonyl]-1H-1,4-diazepine dihydrochloride Using 0.64 g of 1-(tert-butoxycarbonyl)hexahydro-5-methyl-1H-1,4-diazepine prepared by protecting the 1-position of hexahydro-5-methyl-1H-1,4-diazepine synthesized in accordance with U.S. Pat. No. 3,040,029, the procedure of Example 1 was otherwise repeated to provide 0.27 g of the objective compound (white crystals).

m.p. 270–275° C. (decomp.)

Elemental analysis (for $C_{16}H_{21}N_3O_2S.2HCl$) Calcd. (%): C, 48.98; H, 5.91; N, 10.71 Found (%): C, 48.84; H, 6.14; N, 10.63

EXAMPLE 22

Hexahydro-6-methyl-1-[(4-methyl-5-isoquinolinyl) sulfonyl]-1H-1,4-diazepine dihydrochloride Using 0.64 g of hexahydro-6-methyl-1H-1,4-diazepine synthesized in accordance with U.S. Pat. No. 3,040,029, the procedure of Example 1 was otherwise repeated to provide 0.79 g of the objective compound (white crystals).

m.p. 264–271° C. (decomp.)

Elemental analysis (for $C_{16}H_{21}N_3O_2S.2HCl$) Calcd. (%): C, 48.98; H, 5.91; N, 10.71 Found (%): C, 48.98; H, 6.02; N, 10.72

EXAMPLE 23

Cis-2,5-Dimethyl-1-[(4-methyl-5-isoquinolinyl) sulfonyl]piperazine dihydrochloride Using 0.43 g of cis-1-(tert-butoxycarbonyl)-2,5-dimethylpiperazine and 0.48 g of 5-chlorosulfonyl-4-methylisoquinoline, the procedure of Example 1 was otherwise repeated to provide 0.2 g of the objective compound (white crystals).

m.p. 258–263° C. (decomp.)

Elemental analysis (for $C_{16}H_{21}N_3O_2S.2HCl$) Calcd. (%): C, 48.98; H, 5.91; N, 10.71 Found (%): C, 48.69; H, 6.15; N, 10.61

EXAMPLE 24

Hexahydro-5-methyl-1-[(4-methyl-5-isoquinolinyl) sulfonyl]-1H-1,4-diazepine dihydrochloride Using 0.29 g of hexahydro-5-methyl-1H-1,4-diazepine synthesized in accordance with U.S. Pat. No. 3,040,029 and 0.48 g of 5-chlorosulfonyl-4-methylisoquinoline, the procedure of Example 1 was otherwise repeated to provide 0.3 g of the objective compound (white crystals).

m.p. 271–274° C. (decomp.)

Elemental analysis (for $C_{16}H_{21}N_3O_2S.2HCl$) Calcd. (%): C, 48.98; H, 5.91; N, 10.71 Found (%): C, 48.83; H, 6.11; N, 10.46

EXAMPLE 25

6-Fluoro-hexahydro-1-[(4-methyl-5-isoquinolinyl) sulfonyl]-1H-1,4-diazepine hydrochloride Using 0.65 g of 6-fluoro-hexahydro-1H-1,4-diazepine synthesized in accordance with J. Med. Chem., 1990, 33, 142 and 0.72 g of 5-chlorosulfonyl-4-methylisoquinoline, the procedure of Example 1 was otherwise repeated to provide 0.35 g of the objective compound (white crystals).

m.p. 184–185° C. (decomp.)

Elemental analysis (for $C_{15}H_{18}FN_3O_2S.HCl$) Calcd. (%): C, 50.07; H, 5.32; N, 11.68 Found (%): C, 49.86; H, 5.51; N, 11.59

EXAMPLE 26

Hexahydro-2-methyl-1-[(4-methyl-5-isoquinolinyl) sulfonyl]-1H-1,4-diazepine hydrochloride Using 1.07 g of 4-(tert-butoxycarbonyl)-hexahydro-2-methyl-1H-1,4-diazepine prepared by protecting the 4-position of hexahydro-2-methyl-1H-1,4-diazepine (2.8 g) synthesized in accordance with J. Med. Chem., 1990, 33, 142 and 1.21 g of 5-chlorosulfonyl-4-methylisoquinoline, the procedure of Example 1 was otherwise repeated to provide 0.27 g of the objective compound (white crystals).

m.p. 156–162° C. (decomp.)

Elemental analysis (for $C_{16}H_{21}N_3O_2S.HCl$) Calcd. (%): C, 54.00; H, 6.23; N, 11.81 Found (%): C, 53.89; H, 6.38; N, 11.64

EXAMPLE 27

(S)-3-Methyl-1-[(4-methyl-5-isoquinolinyl)sulfonyl] piperazine hydrochloride

Using 0.60 g of (S)-2-methylpiperazine and 0.49 g of 5-chlorosulfonyl-4-methylisoquinoline, the procedure of Example 1 was otherwise repeated to provide 0.66 g of the objective compound (white crystals).

m.p. 270–273° C. (decomp.)

Elemental analysis (for $C_{15}H_{19}N_3O_2S.HCl$) Calcd. (%): C, 52.70; H, 5.90; N, 12.29 Found (%): C, 52.85; H, 5.78; N, 12.39 $[\alpha]_D$: −13.26°

EXAMPLE 28

(R)-3-Methyl-1-[(4-methyl-5-isoquinolinyl)sulfonyl] piperazine hydrochloride

Using 0.50 g of (R)-2-methylpiperazine and 0.40 g of 5-chlorosulfonyl-4-methylisoquinoline, the procedure of Example 1 was otherwise repeated to provide 0.52 g of the objective compound (white crystals).

m.p. 270–273° C. (decomp.)

Elemental analysis (for $C_{15}H_{19}N_3O_2S.HCl.1/2H_2O$) Calcd. (%): C, 51.35; H, 6.03; N, 11.97 Found (%): C, 51.78; H, 6.26; N, 11.71 $[\alpha]_D$: +17.97°

EXAMPLE 29

(S)-2-Methyl-1-[(4-methyl-5-isoquinolinyl)sulfonyl] piperazine hydrochloride

Using 1.0 g of (S)-1-(tert-butoxycarbonyl)-3-methylpiperazine and 1.21 g of 5-chlorosulfonyl-4-methylisoquinoline, the procedure of Example 1 was otherwise repeated to provide 0.85 g of the objective compound (white crystals).

m.p. 271–275° C. (decomp.)

Elemental analysis (for $C_{15}H_{19}N_3O_2S.HCl$) Calcd. (%): C, 52.70; H, 5.90; N, 12.29 Found (%): C, 52.40; H, 5.63; N, 12.00 $[\alpha]_D$: −14.23° (c=1.02, $H_2O$)

EXAMPLE 30

(R)-2-Methyl-1-[(4-methyl-5-isoquinolinyl)sulfonyl] piperazine hydrochloride

Using 0.34 g of (R)-1-(tert-butoxycarbonyl)-3-methylpiperazine and 0.40 g of 5-chlorosulfonyl-4- methylisoquinoline, the procedure of Example 1 was otherwise repeated to provide 0.15 g of the objective compound (white crystals).

m.p. 271–275° C. (decomp.)

Elemental analysis (for $C_{15}H_{19}N_3O_2S \cdot HCl$) Calcd. (%): C, 52.70; H, 5.90; N. 12.29 Found (%): C, 52.37; H, 5.66; N, 12.17

EXAMPLE 31

(R)-(−)-Hexahydro-2-methyl-1-[(4-methyl-5-isoquinolinyl)sulfonyl]-1H-1,4-diazepine hydrochloride Process 1

Using 15.0 g of D-alaninol, the procedures of Reference Example 2 and Example 12 were repeated to provide 1.42 g of the objective compound (white crystals).

m.p. 146–150° C.

Elemental analysis (for $C_{16}H_{21}N_3O_2S \cdot HCl \cdot 3/2H_2O$) Calcd. (%): C, 50.19; H, 6.58; N, 10.97 Found (%): C, 50.15; H, 6.55; N, 10.82 $[\alpha]_D$: −18.05° (c=1.14, $H_2O$)

Process 2

(1) To a solution of 1.0 g of D-alaninol in 50 ml of methylene chloride was added 2.02 g of triethylamine, and after addition of 3.22 g of 5-chlorosulfonyl-4-methylisoquinoline under ice-cooling, the mixture was stirred for 2 hours. This reaction mixture was diluted with water and extracted with methylene chloride and the extract was dried and concentrated. The residue was purified by silica gel column chromatography (chloroform/methanol=30/1) to provide 3.0 g of (R)-2-[(4-methyl-5-isoquinolinyl)sulfonyl amino]-1-propanol (white crystals).

(2) To a solution of 1.1 g of the compound obtained in (1) above in 8 ml of pyridine was added 0.82 g of p-toluenesulfonyl chloride, and the mixture was stirred overnight. The pyridine was then distilled off and the residue was diluted with water, extracted with chloroform, dried, and concentrated. The residue was dissolved in 8 ml of tetrahydrofuran, followed by addition of 0.80 g of 3-amino-1-propanol, and the mixture was stirred at room temperature for 3 hours. The solvent was then distilled off and the residue was purified by silica gel column chromatography (chloroform/methanol/aqueous ammonia=90/10/1) to provide 1.3 g of (R)-3-[N-[2-[[(4-methyl-5-isoquinolinyl)sulfonyl]amino]propyl]amino]-1-propanol (light-yellow oil).

(3) To a solution of 5.8 g of the compound obtained in (2) above in 60 ml of tetrahydrofuran was added 50 ml of 0.1N-aqueous sodium hydroxide solution. Under ice-cooling, a solution of 3.75 g of di-tert-butyl dicarbonate in 40 ml of tetrahydran was added dropwise and the mixture was stirred for 2 hours. The solvent was then distilled off and the residue was extracted with chloroform, dried, and concentrated. The residue was purified by silica gel column chromatography (chloroform/methanol=20/1) to provide 7.34 g of (R)-3-[N-(tert-butoxycarbonyl)-N-[2-[[(4-methyl-5-isoquinolinyl)sulfonyl]amino]propyl]amino]-1-propanol (light-yellow oil).

(4) To a solution of 1.8 g of the compound obtained in (3) above in 30 ml of dry tetrahydrofuran were added 1.62 g of triphenylphosphine and 1.07 g of diethyl azodicarboxylate, and the mixture was heated for 20 minutes. This reaction mixture was concentrated and the residue was dissolved in 30 ml of methylene chloride. To the resulting solution was added 10 ml of tri-fluoroacetic acid under ice-cooling, and the mixture was stirred at room temperature for 1 hour. This reaction mixture was made basic with saturated sodium hydrogencarbonate/$H_2O$, extracted with methylene chloride, dried, and concentrated. The residue was purified by silica gel column chromatography (chloroform/methanol=50/1) and converted to the hydrochloride as in Example 1 (2) to provide 0.9 g of the objective compound (white crystals).

m.p. 146–150° C.

Elemental analysis (for $C_{16}H_{21}N_3O_2S \cdot HCl \cdot 2H_2O$) Calcd. (%): C, 49.03; H, 6.69; N, 10.72 Found (%): C, 48.70; H, 6.69; N, 10.80 $[\alpha]_D$: −17.50° (c=1.11, $H_2O$)

EXAMPLE 32

2-Ethyl-hexahydro-1-[(4-methyl-5-isoquinolinyl)sulfonyl]-1H-1,4-diazepine hydrochloride Using 0.68 g of 1-(tert-butoxycarbonyl)-3-ethyl-hexahydro-1H-1,4-diazepine and 0.72 g of 5-chlorosulfonyl-4-methylisoquinoline, the procedure of Example 1 was otherwise repeated to provide 0.38 g of the objective compound (white crystals).

m.p. 208–210° (decomp.)

Elemental analysis (for $C_{17}H_{23}N_3O_2S \cdot HCl$) Calcd. (%): C, 55.20; H, 6.54; N, 11.36 Found (%): C, 55.30; H, 6.83; N, 11.08

EXAMPLE 33

5,7-Dimethyl-hexahydro-1-[(4-methyl-5-isoquinolinyl)sulfonyl]-1H-1,4-diazepine hydrochloride Using 0.77 g of 5,7-dimethyl-hexahydro-1H-1,4-diazepine and 0.48 g of 5-chlorosulfonyl-4-methylisoquinoline, the procedure of Example 1 was otherwise repeated to provide 0.50 g of the objective compound (white crystals).

m.p. 280–282° C. (decomp.)

Elemental analysis (for $C_{17}H_{23}N_3O_2S \cdot HCl$) Calcd. (%): C, 55.20; H, 6.54; N, 11.36 Found (%): C, 54.96; H, 6.44; N, 11.10

EXAMPLE 34

Hexahydro-1-[(4-methyl-5-isoquinolinyl)sulfonyl]-2-phenyl-1H-1,4-diazepine hydrochloride Using 20.2 g of phenylglycinol, the procedure of Example 12 was otherwise repeated to provide 0.15 g of the objective compound (white crystals).

m.p. 218–221° C.

Elemental analysis (for $C_{21}H_{23}N_3O_2S \cdot HCl \cdot 2H_2O$) Calcd. (%): C, 55.56; H, 6.22; N, 9.26 Found (%): C, 55.55; H, 5.68; N, 9.36

EXAMPLE 35

(R)-(−)-Hexahydro-1-[(1-hydroxy-4-methyl-5-isoquinolinyl)sulfonyl]-2-methyl-1H-1,4-diazepine hydrochloride Using 1.76 g of (R)-(−)-hexahydro-2-methyl-1-[(4-methyl-5-isoquinolinyl)sulfonyl]-1H-1,4-diazepine, the procedure of Example 7 was otherwise repeated to provide 0.65 g of the objective compound (pale yellow crystals).

m.p. 232–235° C. (decomp.)

Elemental analysis (for $C_{16}H_{21}N_3O_3S \cdot HCl \cdot 1/4H_2O$) Calcd. (%): C, 51.06; H, 6.03; N, 11.16 Found (%): C, 51.17; H, 6.08; N, 11.04 $[\alpha]_D$: −32.14° (c=1.04, $H_2O$)

EXAMPLE 36

(S)-(+)-Hexahydro-1-[(1-hydroxy-4-methyl-5-isoquinolinyl)sulfonyl]-7-methyl-1H-1,4-diazepine hydrochloride Using 1.06 g of (S)-(+)-hexahydro-7-methyl-1-[(4-methyl-5-isoquinolinyl)sulfonyl]-1H-1,4-diazepine, the procedure of Example 7 was otherwise repeated to provide 0.30 g of the objective compound (white crystals).

m.p. 215–218° C. (decomp.)

Elemental analysis (for $C_{16}H_{21}N_3O_3S.HCl.3H_2O$) Calcd. (%): C, 45.12; H, 6.63; N, 9.87 Found (%): C, 45.25; H, 6.30; N, 9.52 $[\alpha]_D$: +26.66° (c=1.13, $H_2O$)

EXAMPLE 37

3-[(4-Methyl-5-isoquinolinyl)sulfonyl]-3,6-diazabicyclo[3.2.1]octane hydrochloride Using 3.8 g of 3-benzyl-6-methoxycarbonyl-3,6-diazabicyclo[3.2.1]octane (synthesized in accordance with Japanese Kokai Tokkyo Koho S64-16783), the procedure of Example 9 was otherwise repeated to provide 2.50 g of the objective compound (white crystals).

m.p. 243–245° C.

Elemental analysis (for $C_{16}H_{19}N_3O_2S.HCl.2/3H_2O$) Calcd. (%): C, 52.52; H, 5.88; N, 11.48

Found (%): C, 52.50; H, 5.97; N, 11.04

EXAMPLE 38

6-[(4-Methyl-5-isoquinolinyl)sulfonyl]-3,6-diazabicyclo[3.2.1]octane hydrochloride Using 1.0 g of 3-(tert-butoxycarbonyl)-3,6-diazabicyclo[3.2.1]octane (synthesized in accordance with Japanese Kokai Tokkyo Koho S64-16783), the procedure of Example 10 was otherwise repeated to provide 1.5 g of the objective compound (pale brown crystals).

m.p. 200–205° C.

Elemental analysis (for $C_{16}H_{19}N_3O_2S.HCl.3/2H_2O$) Calcd. (%): C, 50.45; H, 6.09; N, 11.03 Found (%): C, 50.36; H, 6.10; N, 10.89

EXAMPLE 39

3,5-Dimethyl-hexahydro-1-[(4-methyl-5-isoquinolinyl)sulfonyl]-1H-1,4-diazepine hydrochloride To a suspension of 1.5 g of 2,7-dimethyl-hexahydro-1H-1,4-diazepine hydrobromide obtained in Reference Example 3 in 30 ml of pyridine was added 1.58 g of 1,8-diazabicyclo[5.4.0]-7-undecene, and after addition of 0.84 g of 5-chlorosulfonyl-4-methyl-isoquinoline, the mixture was stirred at room temperature for 1 hour. This reaction mixture was concentrated and the residue was diluted with water, extracted with chloroform, dried, and concentrated. The residue was purified by silica gel column chromatography (chloroform/methanol=30/1) and converted to the hydrochloride in the routine manner to provide 0.70 g of the objective compound (white crystals).

m.p. 287–290° C. (decomp.)

Elemental analysis (for $C_{17}H_{23}N_3O_2S.HCl.1/2H_2O$) Calcd. (%): C, 53.89; H, 6.65; N, 11.09 Found (%): C, 53.79; H, 6.47; N, 11.35

EXAMPLE 40

Hexahydro-3-methyl-1-[(4-methyl-5-isoquinolinyl)sulfonyl]-1H-1,4-diazepine hydrochloride Using 0.72 g of hexahydro-2-methyl-1H-1,4-diazepine hydrobromide synthesized as in Example 12, the procedure of Example 39 was otherwise repeated to provide 0.53 g of the objective compound (white crystals).

m.p. 290–294° C. (decomp.)

Elemental analysis (for $C_{16}H_{21}N_3O_2S.HCl.H_2O$) Calcd. (%): C, 51.40; H, 6.47; N, 11.23 Found (%): C, 51.98; H, 6.95; N, 11.18

EXAMPLE 41

(S)-(−)-Hexahydro-7-methyl-1-[(4-methyl-5-isoquinolinyl)sulfonyl]-1H-1,4-diazepine hydrochloride Using 2.0 g of 3-(S)-aminobutan-1-ol (synthesized in accordance with J. Org. Chem., 1977, 42, 1650) in lieu of D-alaninol, and 2-aminoethanol in lieu of 3-amino-1-propanol, the procedure of Example 31 Process 2 was otherwise repeated to provide 1.10 g of the objective compound (white crystals).

m.p. 282–285° C.

Elemental analysis (for $C_{16}H_{21}N_3O_2S.HCl.1/2H_2O$) Calcd. (%): C, 52.67; H, 6.35; N, 11.52 Found (%): C, 52.79; H, 6.19; N, 11.51 $[\alpha]_D$: −1.74° (c=1.03, $H_2O$)

EXAMPLE 42

(R)-(+)-Hexahydro-7-methyl-1-[(4-methyl-5-isoquinolinyl)sulfonyl]-1H-1,4-diazepine hydrochloride Using 2.0 g of 3-(R)-aminobutan-1-ol (synthesized in accordance with J. Org. Chem., 1977, 42, 1650) in lieu of D-alaninol, and 2-aminoethanol in lieu of 3-amino-1-propanol, the procedure of Example 31 Process 2 was otherwise repeated to provide 1.20 g of the objective compound (white crystals).

m.p. 278–282° C. (decomp.)

Elemental analysis (for $C_{16}H_{21}N_3O_2S.HCl.3/2H_2O$) Calcd. (%): C, 50.19; H, 6.58; N, 10.97 Found (%): C, 50.01; H, 6.14; N, 10.91 $[\alpha]_D$: +2.53° (c=1.02, $H_2O$)

EXAMPLE 43

2,2-Dimethyl-hexahydro-1-[(4-methyl-5-isoquinolinyl)sulfonyl]-1H-1,4-diazepine hydrochloride Using 1.30 g of 2-amino-2-methyl-1-propanol in lieu of D-alaninol, and 2-aminoethanol in lieu of 3-amino-1-propanol, the procedure of Example 31 Process 2 was otherwise repeated to provide 0.30 g of the objective compound (white crystals).

m.p. 279–282° C. (decomp.)

Elemental analysis (for $C_{17}H_{23}N_3O_2S.HCl.H_2O$) Calcd. (%): C, 52.63; H, 6.76; N, 10.83 Found (%): C, 52.22; H, 6.83; N, 10.63

EXAMPLE 44

2,7-Dimethyl-hexahydro-1-[(4-methyl-5-isoquinolinyl)sulfonyl]-1H-1,4-diazepine hydrochloride Using 1.0 g of 3-aminobutan-1-ol in lieu of D-alaninol, and 1-amino-2-propanol in lieu of 3-amino-1-propanol, the procedure of Example 31 Process 2 was otherwise repeated to provide 0.60 g of the objective compound (white crystals).

m.p. 256–260° C. (decomp.)

Elemental analysis (for $C_{17}H_{23}N_3O_2S \cdot HCl \cdot 1/2H_2O$) Calcd. (%): C, 53.89; H, 6.65; N, 11.09 Found (%): C, 54.19; H, 6.57; N, 11.14

EXAMPLE 45

(R)-(+)-Hexahydro-5-methyl-1-[(4-methyl-5-isoquinolinyl)sulfonyl]-1H-1,4-diazepine hydrochloride Using 0.83 g of 2-aminoethanol in lieu of D-alaninol, and 3-(R)-aminobutan-1-ol (synthesized in accordance with J. Org. Chem., 1977, 42, 1650) in lieu of 3-amino-1-propanol, the procedure of Example 31 Process 2 was otherwise repeated to provide 0.41 g of the objective compound (white crystals).

m.p. 284–288° C.

Elemental analysis (for $C_{16}H_{21}N_3O_2S \cdot HCl \cdot 1/2H_2O$) Calcd. (%): C, 52.67; H, 6.35; N, 11.52 Found (%): C, 52.36; H, 6.10; N, 11.37 $[\alpha]_D$: +3.61° (c=1.05, $H_2O$)

EXAMPLE 46

(S)-(−)-Hexahydro-5-methyl-1-[(4-methyl-5-isoquinolinyl)sulfonyl]-1H-1,4-diazepine hydrochloride Using 0.50 g of 2-aminoethanol in lieu of D-alaninol, and 3-(S)-aminobutan-1-ol (synthesized in accordance with J. Org. Chem., 1977, 42, 1650) in lieu of 3-amino-1-propanol, the procedure of Example 31 Process 2 was otherwise repeated to provide 0.27 g of the objective compound (white crystals).

m.p. 283–284° C.

Elemental analysis (for $C_{16}H_{21}N_3O_2S \cdot HCl \cdot H_2O$) Calcd. (%): C, 51.40; H, 6.47; N, 11.23 Found (%): C, 51.28; H, 6.16; N, 11.11 $[\alpha]_D$: −4.00° (c=1.10, $H_2O$)

EXAMPLE 47

(S)-(+)-2-(4-Aminobutyl)-hexahydro-1-[(4-methyl-5-isoquinolinyl)sulfonyl]-1H-1,4-diazepine trihydrochloride (1) Under argon gas, 20 ml of 1M borane-tetrahydrofuran complex was added dropwise to a solution of 5.0 g of N-α-tert-butoxycarbonyl-N-ε-benzyloxycarbonyl-L-lysine in 3 ml of tetrahydrofuran with ice-cooling and the mixture was stirred at room temperature for 1.5 hours. To this reaction mixture was added 10 ml of water-tetrahydrofuran, and after the aqueous layer was saturated with anhydrous potassium carbonate, the organic layer was discarded. The aqueous layer was extracted with ether three times and the extract was dried and concentrated. The residue was dissolved in ethyl acetate, followed by addition of 25% HCl/ethyl acetate under ice-cooling. The mixture was stirred at room temperature for 2 hours and then concentrated to provide 2.15 g of (S)-2-amino-6-(benzyloxycarbonylamino)-1-hexanol (colorless oil).

(2) Using 2.15 g of the compound obtained in (1) above in lieu of D-alaninol, the procedure of Example 31 Process 2 was otherwise repeated to provide 0.47 g of the objective compound (white crystals).

m.p. 232–240° C. (decomp.)

Elemental analysis (for $C_{19}H_{28}N_4O_2S \cdot 3HCl \cdot 9/2H_2O$) Calcd. (%): C, 40.25; H, 7.11; N, 9.88 Found (%): C, 40.03; H, 7.67; N, 9.74 $[\alpha]_D$: +30.68° (c=1.15, $CH_3OH$)

Formulation Example 1

Recipe (per ml)

| | |
|---|---|
| Compound of Example 21 | 3 mg |
| Sodium chloride | 9 mg |
| Water for injection | q.s. |
| | 1 ml |

Preparation Protocol

Dissolve the Compound of Example 26 and sodium chloride in water for injection, filter the solution through a membrane filter (0.22 μm), fill the filtrate in ampules, and sterilize to provide an aqueous injection.

Formulation Example 2

Recipe (per vial)

| | |
|---|---|
| Compound of Example 26 | 3 mg |
| Mannitol | 50 mg |

Preparation Protocol

Dissolve the compound of Example 26 and mannitol in water for injection, filter the solution aseptically through a membrane filter (0.22 μm), fill the filtrate in vials, and lyophilize in the routine manner to provide an injection for extemporaneous reconstitution.

Formulation Example 3

Recipe (in 180 mg per tablet)

| | |
|---|---|
| Compound of Example 31 | 10 mg |
| Lactose | 100 mg |
| Corn starch | 55 mg |
| Low-substitution hydroxypropylcellulose | 9 mg |
| Polyvinyl alcohol (partial hydrolysate) | 5 mg |
| Magnesium stearate | 1 mg |

Preparation Protocol

Mix the above components other than polyvinyl alcohol and magnesium stearate uniformly and wet-granulate the mixture using an aqueous solution of polyvinyl alcohol as the binder to prepare granules for compression. Mix magnesium stearate with the above granulation and, using a compression tablet machine, mold the composition into oral tablets each weighing 180 mg.

Formulation Example 4

Recipe (in 220 mg per capsule)

| | |
|---|---|
| Compound of Example 45 | 10 mg |
| Lactose | 187 mg |
| Microcrystalline cellulose | 20 mg |
| Magnesium stearate | 3 mg |
| | 220 mg |

Preparation Protocol

Mix the above components uniformly and, using a capsule filling machine, fill the mixture into hard capsule shells, 220 mg per capsule, to provide hard capsules.

Formulation Example 5
Recipe (in each 1 g of granules)

| | |
|---|---|
| Compound of Example 26 | 10 mg |
| Lactose | 880 mg |
| Low-substitution hydroxypropylcellulose | 70 mg |
| Hydroxypropylcellulose | 40 mg |
| | 1000 mg |

Preparation Protocol

Mix the above components other than hydroxypropylcellulose uniformly, knead the mixture using an aqueous solution of hydroxypropylcellulose as the binder, and granulate the kneadings with a granulating machine to provide granules.

Test Example 1

Effect on the Calcium Ionophore-Induced Contraction of the Rat Aorta

Rats (SD, male, 10–14 weeks old) were sacrificed by exsanguination under ether anesthesia and the thoracic aorta (ca 3 cm) was isolated. After removal of the fat and connective tissue, the isolated aorta was sliced into rings about 3 mm in width. The luminal wall of the ring-shaped aortic preparation was rubbed to remove the endothelial cells. This preparation was suspended to the isometric tension transducer of a Magnus equipment containing an organ bath medium and loaded with a static tension of 1 g. The Magnus bath was maintained at 37° C. under aerated with a mixed gas (95% $O_2$+5% $CO_2$) and, with the organ bath replaced with fresh one at intervals of about 20 minutes, the aortic preparation was equilibrated for about 1 hour. To this preparation, calcium ionophore A23187 was added at a final concentration of 1 $\mu M$, and after the constant contractile responses of the aortic preparation were confirmed, the test compound was cumulatively administered. The contraction-relaxation response during the time was recorded and the 50% inhibitory concentration [$IC_{50}$ ($\mu M$)] of the test compound against A23187-induced vascular contraction was determined. As a result, the $IC_{50}$ values of the compounds of Example 12 and Example 26 were found to be 1.1 and 0.74, respectively. On the other hand, the $IC_{50}$ value of the positive control fasudil hydrochloride was 5.1. The composition of the organ bath used in this experiment was: NaCl 115.9 mM (the same applies below); KCl 5.9; $CaCl_2$ 2.5; $MgCl_2$ 1.2; $NaH_2PO_4$ 1.2; $NaHCO_3$ 25.0; glucose 11.5. Those components were dissolved in deionized distilled water. The pH of the organ bath saturated with said mixed gas was 7.4.

The compound of the invention has the action to relieve the contractile response of blood vessels to calcium ionophore and the intensity of the action was remarkably high as compared with fasudil hydrochloride.

Test Example 2

Rat Middle Cerebral Arterial Blood Flow-Increasing Effect

Using rats (SD, male, 11–12 weeks old) under urethane anesthesia, the head of each animal was fixed and the skin of the left buccal region was incised. After the buccinator muscle was removed, the zygomatic bone was exposed. In the cranial bone, immediately above the middle cerebral artery (MCA), a hole about 5 mm in diameter was drilled using an electric dental drill for allowing direct visual access to the MCA. The probe (diameter: 1.0 mm) of a laser Doppler blood flowmeter was placed in close proximity with the MCA to monitor the change in MCA blood flow. The test compound was dissolved and diluted in saline and 3 mg/kg was administered via a cannula from the femoral vein. The dose volume was adjusted to 0.1 ml/100 g and the whole amount was administered over about 30 seconds. The effect of each test compound was expressed as the percent increase in blood flow from the pre-administration baseline and the duration of action was expressed in the period of time till return to the baseline. As a result, the compound of the invention was equivalent to fasudil hydrochloride in the percent increase in blood flow but was by far superior to fasudil hydrochloride in the duration of action. Thus, whereas the duration of action of fasudil hydrochloride was 2.3 minutes, those of the compound of Example 26 and Example 31 were 31.2 minutes and 36.0 minutes, respectively.

The compound of the invention has the action to increase the rat middle cerebral arterial blood flow and the duration of this action was by far longer than that of fasudil hydrochloride.

Test Example 3

Cerebral Vasospasm-Relieving Effect in the Rat Model of Subarachnoid Hemorrhage

With rats (SD, male, 11–12 weeks old) fixed in prone position under pentobarbital anesthesia, a midline incision was made in the dorsocervical region. Then, 0.20 ml of cerebrospinal fluid was removed from the cranial cavity by cervical vertebral paracentesis and 0.30 ml of arterial blood from another rat was infused into the cisterna magna. Then, the head was tilted down through an angle of 20 degrees for 20 minutes to allow the blood to be distributed uniformly from the basilar artery to Willis' cords. On the following day, with the animal fixed in supine position under urethane anesthesia, the cervical region was incised for tracheal cannulation. After the occipital bone was exposed, the dura mater, arachnoid, and pia mater were incised to expose the basilar artery. After the incision was covered with liquid paraffin, the basilar artery was recorded under microscopic magnification on a video recorder and the diameter of the basilar artery was determined by image analysis. The test compound was administered in a dose of 3 mg/kg from the left femoral vein over 1 minute. The effect of each compound was expressed in the percent increase in diameter at the maximum relaxation time as compared with the pre-administration baseline. As a result, whereas the compounds of Example 1 and Example 21 caused increases of 21.4% and 15.1%, respectively, in basilar artery diameter, fasudil hydrochloride caused only an increase of 7.5%.

Test Example 4

Cerebral Vasospasm-Relieving Effect in the Canine Model of Subarachnoid Hemorrhage According to the method of Varsos et al. [J. Neurosurgery, 58, 11–17, 1983], a two-hemorrhage canine model was developed by twice injection of autologous blood into the cisterna magna. On day 1 of experiment, a control angiogram of the basilar artery prior to medication was recorded under pentobarbital anesthesia. Then, 4 ml of cerebrospinal fluid was removed from the cisterna magna and the same volume of autologous blood was injected at a rate of 2 ml/min. After this blood injection, the head was tilted down through an angle of 30 degrees for 30 minutes to allow the blood to be distributed uniformly throughout Willis' cords. On day 3 of experiment, 4 ml of autologous blood was injected again into the cisterna magna. On day 7, a cerebral angiogram was taken under pentobarbital anesthesia to verify the induction of delayed cerebral vasospasm and the evaluation of the drug was then carried out. The test compound, 3 mg/kg, was administered from the left femoral vein over 1 minute. Angiography was performed immediately before drug administration and 10, 20, 30, and 60 minutes after the start of administration. The action of each test compound was expressed in the percent increase in maximal sectional area of the basilar artery as compared with the baseline value prior to administration. As a result, the percent increases obtained with the compounds of Example 21, Example 26, and Example 31 were found to be 27.9%, 37.1%, and 34.1%, respectively. On the other hand, the percent increase with the positive control fasudil hydrochloride was 9.1%. Thus, compared with fasudil hydrochloride, the compound of the invention showed very potent vasospasm-reversing activity and caused recovery of the caliber of the basilar artery substantially to the pretreatment baseline value in the canine model of subarachnoid hemorrhage.

Test Example 5

Prophylactic Effect on Rat Cerebral Vasospasm

Rats (SD, male, 11–13 weeks old) were fixed in prone position under pentobarbital anesthesia and a midline incision was made in the dorsocervical region. After 0.2 ml of cerebrospinal fluid was removed from the cranial cavity by cervical vertebral paracentesis, 0.30 ml of either artificial cerebrospinal fluid or rat arterial blood was injected into the cisterna magna over 1 minute. Then, the head was tilted down through 20 degrees for 10 minutes to allow the basilar arterial blood to be distributed uniformly in Willis' cords. The incision was treated with Terramycin and sutured and 10 mg of Viccillin was administered intramuscularly. After 24 hours, the rat was anesthetized with urethane (1.1 g/kg, i.p.) and fixed in supine position. The brain tissue was fixed by retrograde perfusion with PBS/formalin from the descending aorta and stained by infusing 0.8 ml of Monastral Blue from the descending aorta. After the brain was removed, the basilar arterial region was photographed and the diameter of the basilar artery was determined. The drug was dissolved in saline and administered over 1 minute into the right femoral vein 20 minutes after blood injection.

As a result, the group treated with 3 mg/kg i.v. of the compound of Example 31 showed no evidence of the basilar artery vasospasm which was otherwise induced at 24 hours after blood infusion. With the positive control fasudil hydrochloride, the basilar artery vasospasm at 24 hours after blood injection was not observed in the group treated with 10 mg/kg i.v.

Test Example 6

Effect on Cerebral Infarction in the Rat Model of Transient Middle Cerebral Artery Occlusion With male rats (Slc:SD strain, 7 weeks old) anesthesized with halothane, the common carotid artery was incised and a nylon thread was inserted from the incision and advanced through the internal carotid artery to the origin of the middle cerebral artery. After this arrest of middle cerebral arterial blood flow, the anesthesia was terminated and 2 hours later the nylon thread was removed for reperfusion. After 6 hours of reperfusion, the brain was removed and stained with triphenyltetrazolium chloride (TTC) for identification of the infarcted region. The infarct volume was determined for each of the cerebral cortex and the striatum. The drug was administered intravenously over 1 minute for a total of 3 times, i.e. 30 minutes before occlusion of the middle cerebral artery, immediately after occlusion, and one hour later. Saline was administered as a control. The results were expressed in mean ± standard error and analyzed for significant difference by the Dunnett method. As a result, the compound of Example 31, administered three times at each dose of 0.1 or 0.3 mg/kg and the compound of Example 26, administered three times at 0.1 mg/kg respectively showed significant protection against infarction in both the cerebral cortex and the striat. On the other hand, fasudil hydrochloride administered three times at 5 mg/kg showed significant antiinfarct effect for the striate body only.

Test Example 7

Effect on Cerebral Infarction in the Rat Model of Photochemically Induced Thrombotic (PIT) Middle Cerebral Artery Occlusion Male rats (Slc:SD strain, 7 weeks old) were inhalation-anesthetized with a 1–2% halothane-containing mixed gas (nitrous oxide:oxygen=70:30) and using an electric dental drill, a hole about 5 mm in diameter was drilled in the cranial bone immediately above the middle cerebral artery (MCA) to provide a direct visual access to the MCA. Rose Bengal (RB), 20 mg/kg, was administered intravenously. After 5 minutes, using a three-dimensional manipulator, a light guide (diameter 3.0 mm) as a light source for generating thrombosis was brought close to the MCA for irradiating the artery with green light for 10 minutes. After 24 hours, the animal was decapitated and the brain was removed. Coronal sections at 2 mm intervals were prepared and stained with TTC and the infarct volume for the whole brain was determined. The drug was administered intravenously over 1 minute for a total of 3 times, i.e. immediately after completion of green-light irradiation and 1 and 2 hours later. Saline was administered in a same way as a control. The results were expressed in mean ± standard error and analyzed for significant difference by the Dunnett method. As a result, the compound of Example 31 showed a significant antiinfarct effect at the dose of 0.3 or 3 mg/kg×3. On the other hand, fasudil hydrochloride showed a significant antiinfarct effect at 10 mg/kg×3.

Test Example 8

Acute Toxicity

Using 5-week-old male ddY mice (6 per group), the test drug was administered over 60 seconds from the caudal vein and the animal was observed for mortality over the subsequent 24-hour period. The test drug was used as dissolved and diluted in saline or dimethyl sulfoxide (DMSO). As the test drugs, the compounds of Example 1, Example 21, Example 22, and Example 24 and fasudil hydrochloride were used. As a result, none of the compounds of the invention and fasudil hydrochloride caused death at the dose of 40 mg/kg.

INDUSTRIAL APPLICABILITY

Thus, compared with the control fasudil hydrochloride, the compound of the invention showed sufficient cerebral vasospasm-reversing activity in much lower dose. Moreover, the duration of action of the compound of the invention was also considerably longer. Those findings suggest the usefulness of the compound of the invention in the prevention and treatment of cerebrovascular diseases, particularly brain tissue impairments due to the cerebral vasospasm subsequent to cerebral hemorrhage. Furthermore, the compound of the invention has cerebral vasodilating activity and protectant activity against ischemic neuronal death, thus being useful for the management of sequelae of cerebral hemorrhage, cerebral infarction, transient cerebral ischemic attack, or head trauma.

What is claimed is:

1. A compound of formula [I],

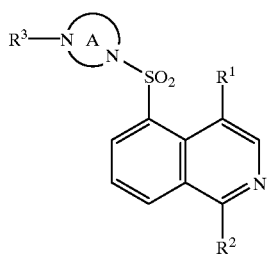

[I]

where
- $R^1$ is alkyl, alkenyl, alkynyl, alkoxy, hydroxy, cyano, or halogen;
- $R^2$ is hydrogen, hydroxy, or halogen;
- $R^3$ is hydrogen, alkyl, or amidino; and
- Ring A is a 5 to 11-membered cyclic amino group which may be bridged between two carbon atoms in optional positions and which may be substituted, or
- a pharmaceutically acceptable salt, hydrate or solvate thereof.

2. The compound according to claim 1, wherein $R^1$ is alkyl.

3. The compound according to claim 2, wherein the alkyl is straight-chain or branched of 1–6 carbon atoms.

4. The compound according to claim 3, wherein the alkyl includes 1–4 carbon atoms.

5. The compound according to claim 3, wherein the alkyl is selected from the group consisting of methyl, ethyl, n-propyl, isopropyl, n-butyl, isobutyl, sec-butyl, tert-butyl, n-pentyl, isopentyl, n-hexyl, and isohexyl.

6. The compound according to claim 5, wherein the alkyl is methyl.

7. The compound according to claim 1, wherein $R^2$ is hydrogen.

8. The compound according to claim 1, wherein $R^3$ is hydrogen.

9. The compound according to claim 1, wherein ring A is hexahydro-1H-1,4-diazepin-1-yl, the ring carbon atom or atoms of which may be substituted by an alkyl moiety.

10. The compound according to claim 9, wherein ring A is selected from the group consisting of 2-methyl-hexahydro-1H-1,4-diazepinyl or 7-methyl-hexahydro-1H-1,4-diazepinyl.

11. The compound according to claim 1, wherein the compound is selected from the group consisting of hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl)sulfonyl]-1H-1,4-diazepine hydrochloride, hexahydro-7-methyl-1-[(4-methyl-5-isoquinolinyl)sulfonyl]-1H-1,4-diazepine dihydrochloride, hexahydro-5-methyl-1-[(4-methyl-5-isoquinolinyl)sulfonyl]-1H-1,4-diazepine dihydrochloride, hexahydro-2-methyl-1-[(4-methyl-5-isoquinolinyl)sulfonyl]-1H-1,4-diazepine hydrochloride, (R)-(−)-hexahydro-2-methyl-1-[(4-methyl-5-isoquinolinyl)sulfonyl]-1H-1,4-diazepine hydrochloride and (R)-(+)-hexahydro-5-methyl-1-[(4-methyl-5-isoquinolinyl)sulfonyl]-1H-1,4-diazepine hydrochloride.

12. A pharmaceutical composition useful for treating cerebrovascular disease comprising a therapeutically effective amount of the compound of claim 1, in combination with a pharmaceutically acceptable carrier or diluent.

13. A method of reducing the risk of cerebral vasospasm following a subarachanoid hemorrhage in a subject at risk, comprising administering to the subject the compound of claim 1 in combination with a pharmaceutically acceptable carrier or diluent in an amount effective to reduce the risk of cerebral vasospasm in the subject.

14. A method of treating a subject suffering from a cerebrovascular disease, comprising administering to the subject the compound of claim 1 in combination with a pharmaceutically acceptable carrier or diluent in an amount sufficient to treat the subject.

15. A method of inhibiting or preventing cerebral vasospasm following a subarachanoid hemorrhage in a subject at risk, comprising administering to the subject the compound of claim 1 in combination with a pharmaceutically acceptable carrier or diluent in an amount sufficient to inhibit or prevent the cerebral vasospasm in the subject.

16. A method for increasing cerebral blood flow volume in a subject comprising administering to the subject the compound of claim 1 in combination with a pharmaceutically acceptable carrier or diluent in an amount sufficient to increase cerebral blood flow in the subject.

* * * * *